(12) United States Patent
Lathers et al.

(10) Patent No.: US 10,925,755 B2
(45) Date of Patent: Feb. 23, 2021

(54) OSSEOINTEGRATABLE PROSTHETIC DEVICE AND MANUFACTURING METHOD

(71) Applicants: Steven Lathers, Englewood, CO (US); Jeffrey La Belle, Tempe, AZ (US)

(72) Inventors: Steven Lathers, Englewood, CO (US); Jeffrey La Belle, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 341 days.

(21) Appl. No.: 15/678,584

(22) Filed: Aug. 16, 2017

(65) Prior Publication Data

US 2018/0049897 A1 Feb. 22, 2018

Related U.S. Application Data

(60) Provisional application No. 62/376,184, filed on Aug. 17, 2016.

(51) Int. Cl.
*A61F 2/78* (2006.01)
*A61F 2/50* (2006.01)

(52) U.S. Cl.
CPC ............. *A61F 2/78* (2013.01); *A61F 2/5044* (2013.01); *A61F 2/5046* (2013.01); *A61F 2002/7887* (2013.01)

(58) Field of Classification Search
CPC .......... A61F 2/30749; A61F 2002/7887; A61F 2002/30858
See application file for complete search history.

(56) References Cited

U.S. PATENT DOCUMENTS 4,634,422 A * 1/1987 Kantrowitz ....... A61M 39/0247
435/379
4,883,491 A * 11/1989 Mallory ............. A61F 2/30734
623/22.31

(Continued)

OTHER PUBLICATIONS

Tariverdian et al., Scaffold for bone tissue engineering, 2019, Elsevier Ltd., Chapter 10, pp. 198-202 (Year: 2019).*

(Continued)

*Primary Examiner* — Bruce E Snow
*Assistant Examiner* — Melissa A Hoban
(74) *Attorney, Agent, or Firm* — Withrow & Terranova, P.L.L.C.

(57) ABSTRACT

An osseointegratable prosthetic device suitable for implantation via a one-step surgical process includes a threaded insertion end, an externally accessible tool interface end, and an intermediately arranged scaffold portion defining recesses that permit ingrowth of skeletal tissue. Such recesses may include multiple longitudinal fins as well as transverse ribs, which may embody or be coated with porous material to promote bone ingrowth. A split flange portion includes discontinuous portions and may permit pretensioning of the device. The device may be fabricated as a unitary body structure from thermoplastic materials using techniques such as fused filament fabrication (a form of 3D printing). The osseointegratable prosthetic device enables one-step surgical implantation without requiring separately implantable fixture/sleeve and abutment portions according to conventional osseointegratable prosthetics. Methods for fabricating an osseointegratable prosthetic device are further provided.

24 Claims, 33 Drawing Sheets

(56) References Cited

U.S. PATENT DOCUMENTS

| | | | | |
|---|---|---|---|---|
| 5,061,181 | A | * | 10/1991 | Niznick ............... A61C 8/0022 433/174 |
| 5,876,457 | A | * | 3/1999 | Picha ..................... A61F 2/446 623/17.11 |
| 8,454,363 | B2 | * | 6/2013 | Worthington ........ A61C 8/0001 433/174 |
| 8,641,778 | B2 | * | 2/2014 | Mann ..................... A61B 17/60 623/32 |
| 9,308,103 | B1 | * | 4/2016 | Kluger ..................... A61F 2/80 |
| 9,668,889 | B2 | * | 6/2017 | Holt ......................... A61F 2/78 |
| 2006/0260534 | A1 | * | 11/2006 | Petrakis ................... G01K 1/02 116/216 |
| 2011/0045439 | A1 | * | 2/2011 | Tripodakis .............. A61L 27/06 433/174 |
| 2011/0190907 | A1 | * | 8/2011 | Porter ....................... A61F 2/78 623/32 |
| 2013/0166009 | A1 | * | 6/2013 | Branemark ........... A61F 2/2814 607/149 |
| 2014/0081422 | A1 | * | 3/2014 | Hugate ............... A61F 2/30771 623/32 |
| 2016/0331422 | A1 | * | 11/2016 | Al Muderis ....... A61B 17/7233 |
| 2017/0172488 | A1 | * | 6/2017 | Kantrowitz .......... A61B 5/0531 |
| 2017/0304073 | A1 | * | 10/2017 | Pedoulias .............. A61B 17/68 |

OTHER PUBLICATIONS

Chiu, J., et al., "Prediction of upper extremity impact forces during falls on the outstretched hand," Journal of Biomechanics, vol. 31, Dec. 1998, 8 pages.

Lathers, S., et al., "Advanced Manufactured Fused Filament Fabrication 3D Printed Osseointegrated Prosthesis for a Transhumeral Amputation Using Taulman 680 FDA," 3D Printing and Additive Manufacturing, vol. 3, No. 3, Sep. 1, 2016, 9 pages.

Welke, B., et al., "Stiffness and ultimate load of osseointegrated prosthesis fixations in the upper and lower extremity," BioMedical Engineering OnLine, vol. 12, No. 70, Jul. 2013, 13 pages.

* cited by examiner

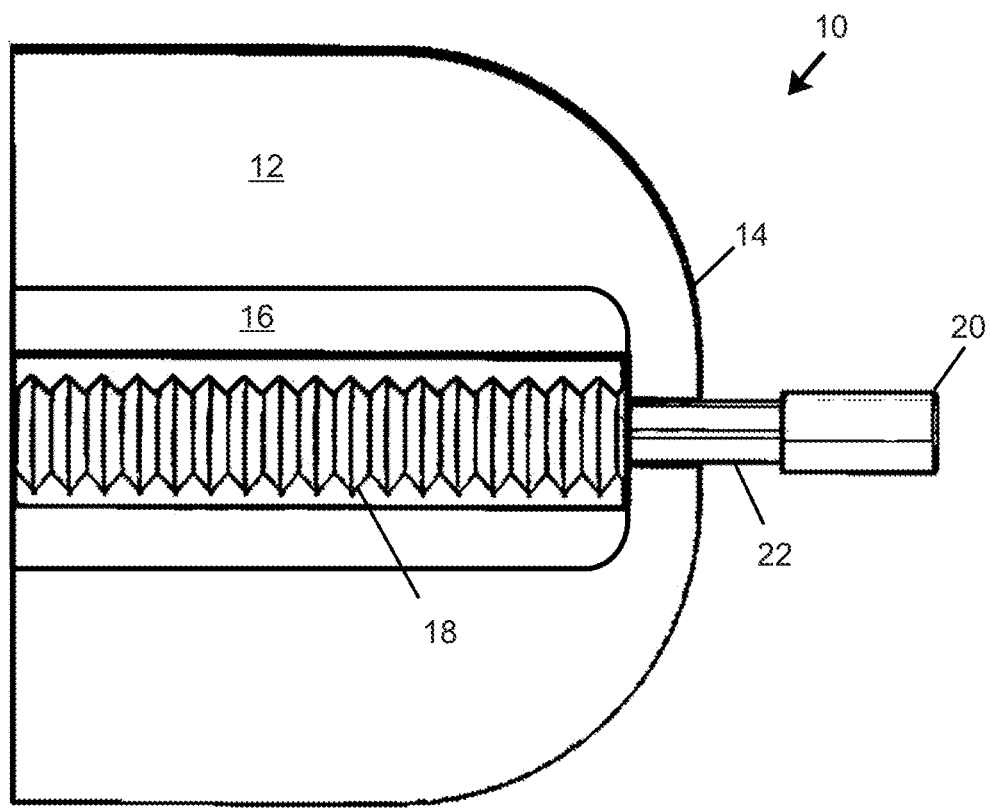
FIG._1
(RELATED ART)

| Polyamide (nylon) | Repeating unit |
|---|---|
| 6 | 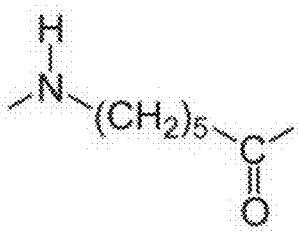 |
| 6,6 | 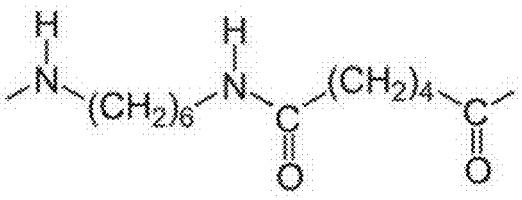 |
| 6,10 | 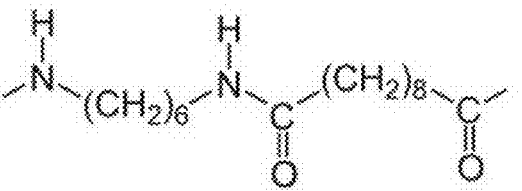 |
| 11 | 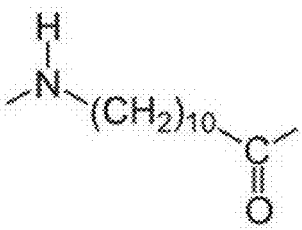 |
| 12 | 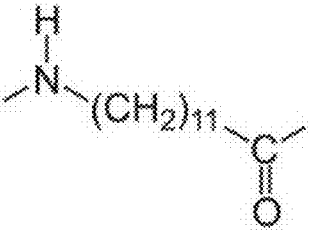 |
FIG._2

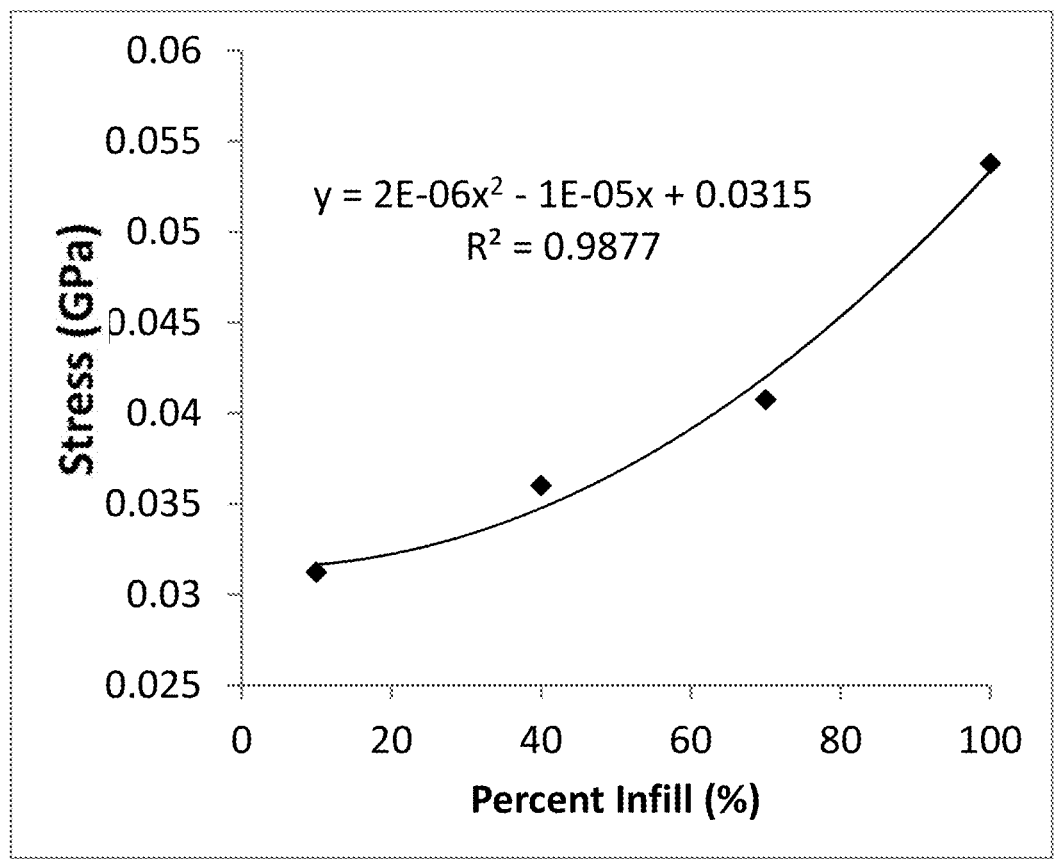
FIG._3B
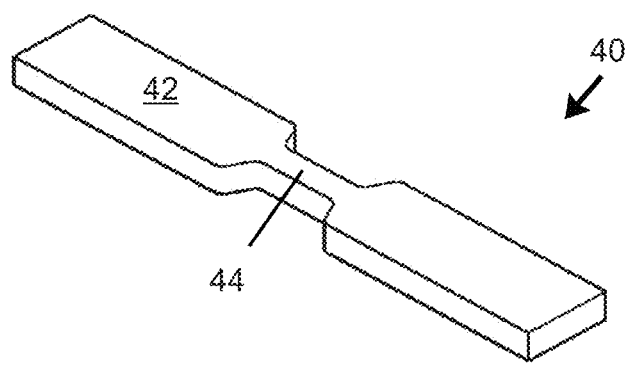
FIG._3C

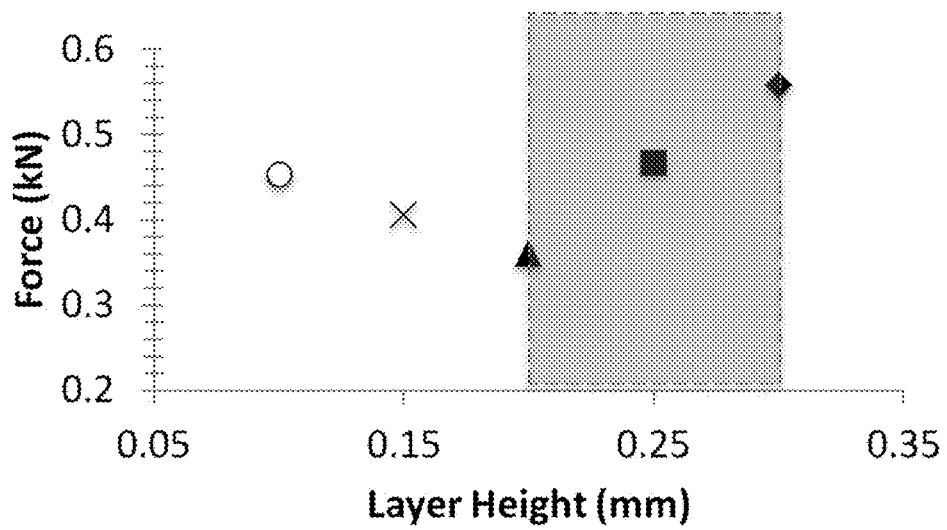
FIG._3E
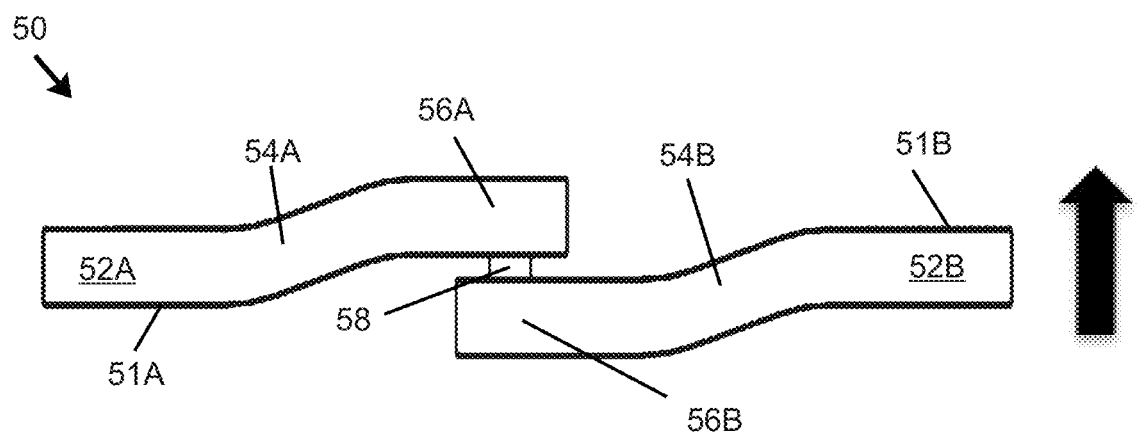
FIG._3F
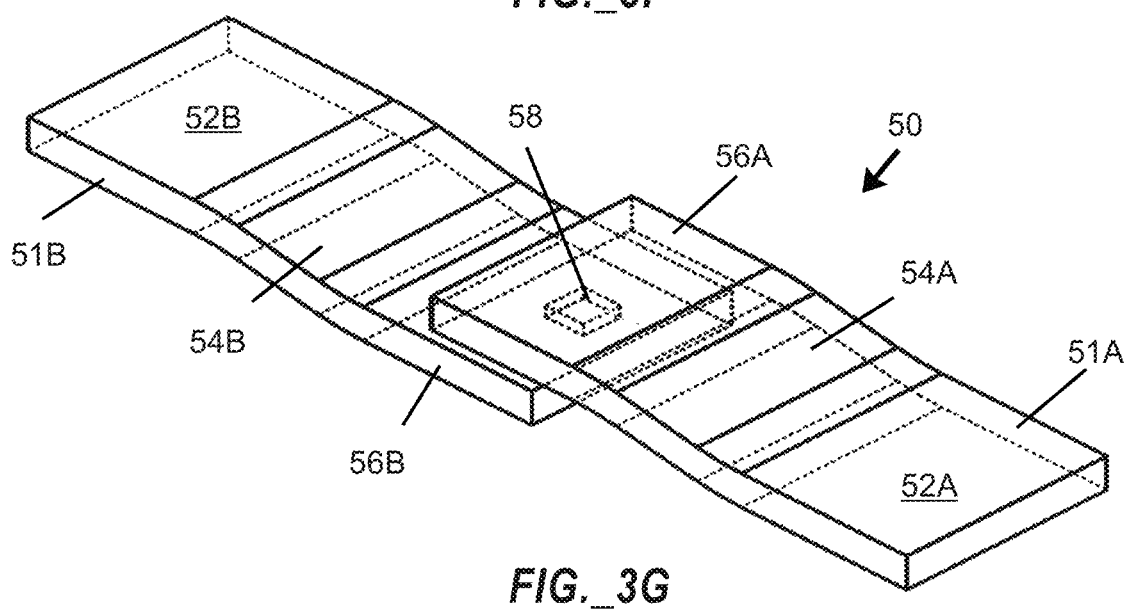
FIG._3G

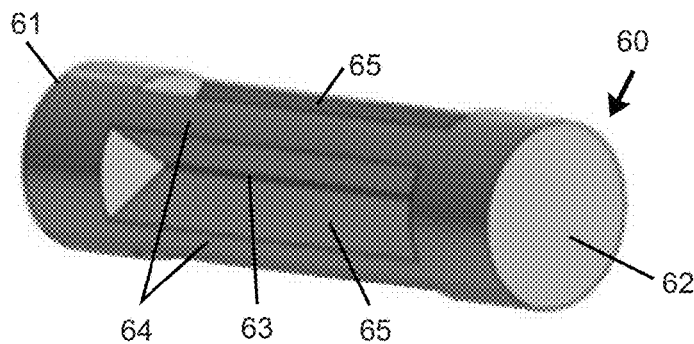
FIG._4A
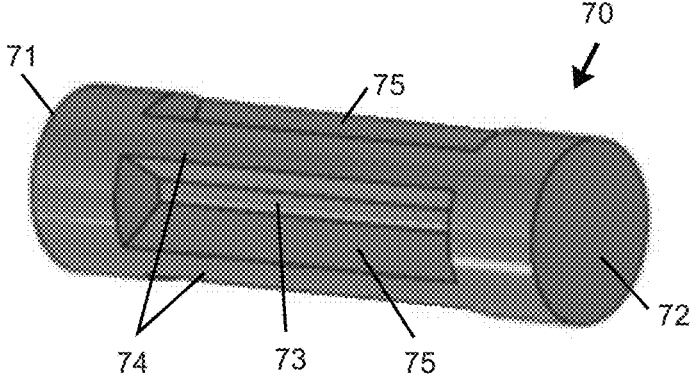
FIG._4B
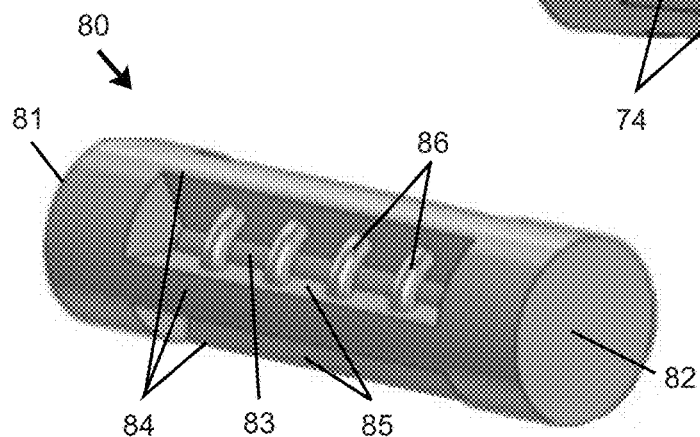
FIG._4C
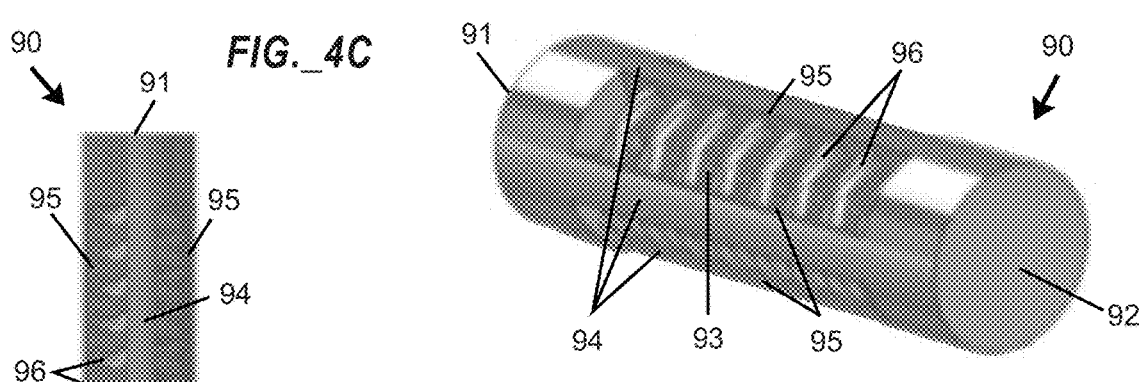
FIG._4D
FIG._4E

|  | Δ Stress (%) | | Δ Displacement (%) | |
| --- | --- | --- | --- | --- |
|  | Tension | Bending | Tension | Bending |
| Fins only (Baseline) | 0.00 | 0.00 | 0.00 | 0.00 |
| Fins with center rod | −95.60 | 1.45 | −89.65 | −9.58 |
| Fins with center rod and ribs | 3.21 | 1.67 | −10.34 | −10.62 |
| Rod and double helix | 24.09 | −99.83 | −3.65 | −99.82 |

FIG. 4F

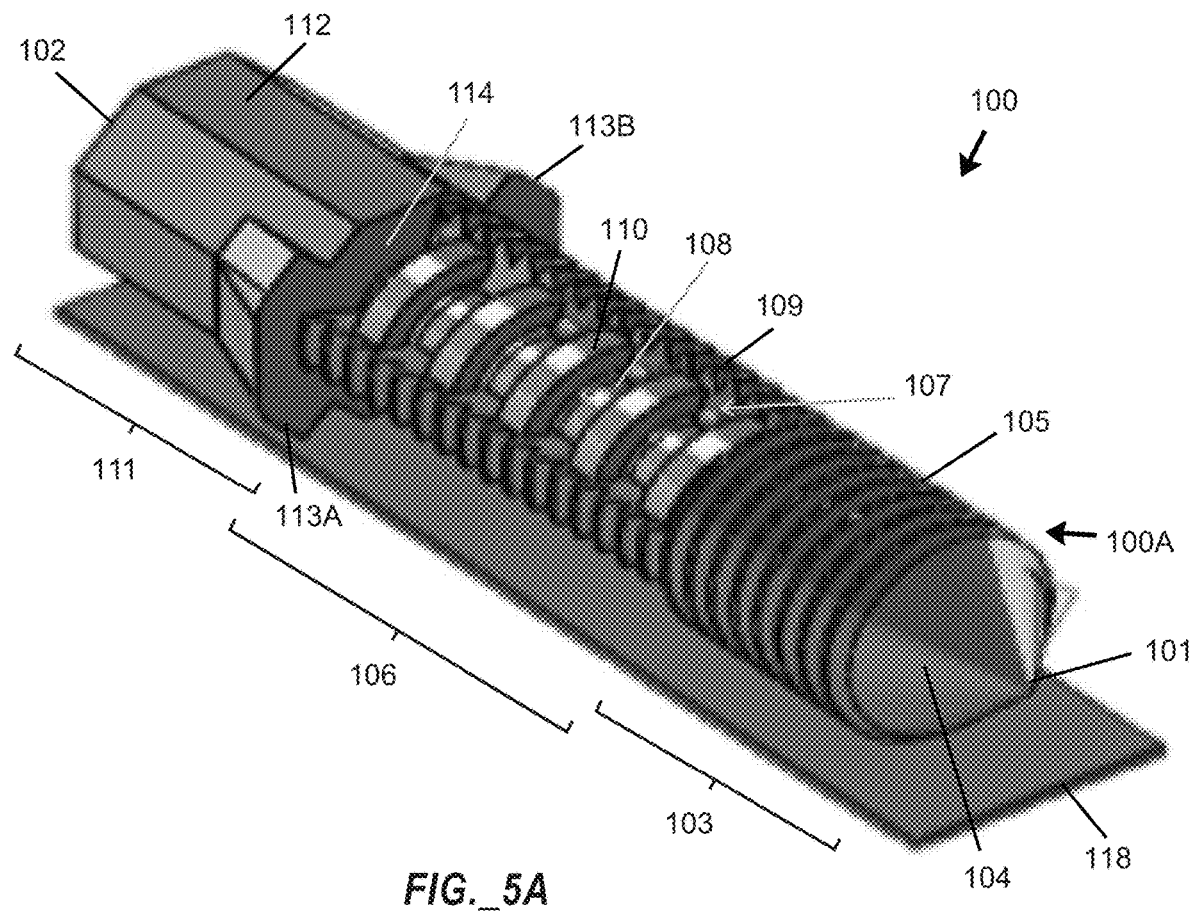
FIG._5A
| Flange contact area | 115.17mm^2 |
| Voided Volume Space | 3910.254mm^3 |
| Total Volume of 40mm height of scaffolding area | 12566.371mm^3 |
| Screw Head Length | 25.0mm |
| Anchor Length | 30.0mm |
FIG._5B

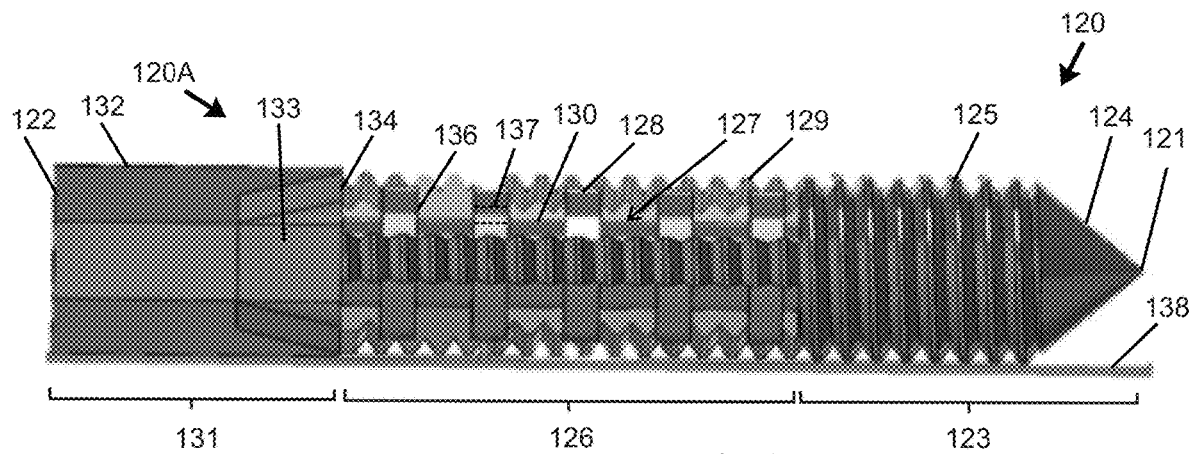
FIG._6A
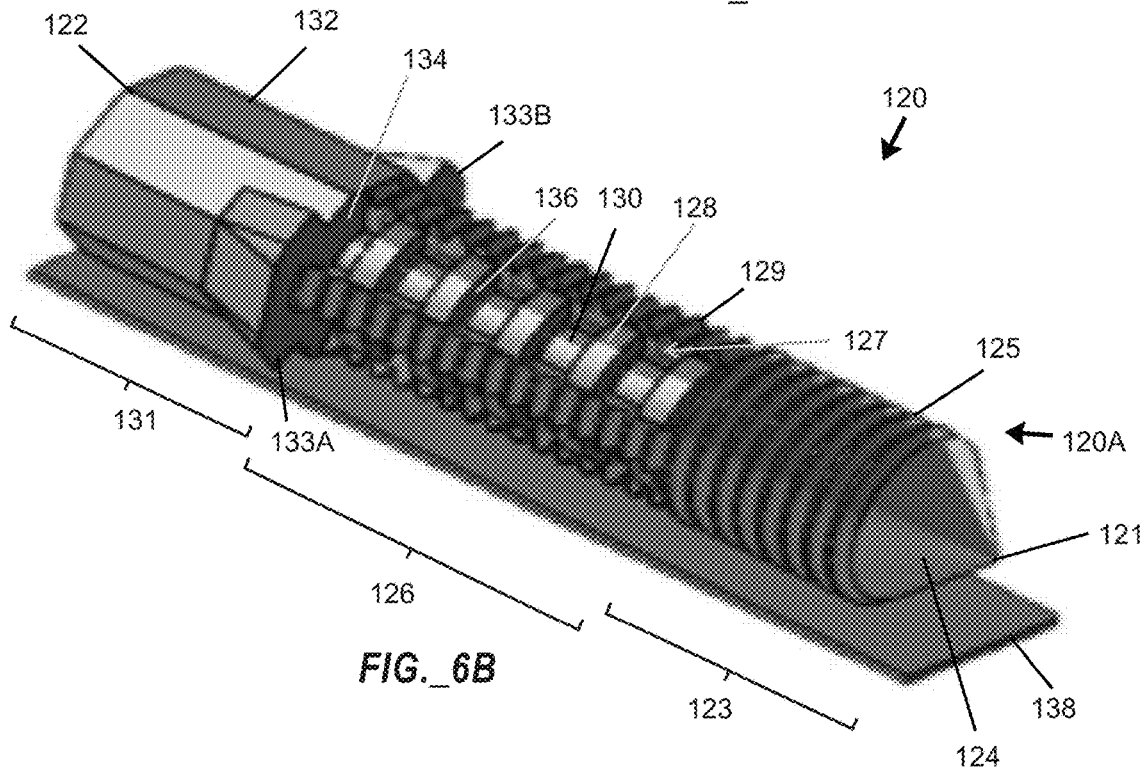
FIG._6B
| Flange contact area | 115.17mm^2 |
| Voided Volume Space | 3501.504mm^3 |
| Total Volume of 40mm height of scaffolding area | 12566.371mm^3 |
| Screw Head Length | 25.0mm |
| Anchor Length | 30.0mm |
FIG._6C

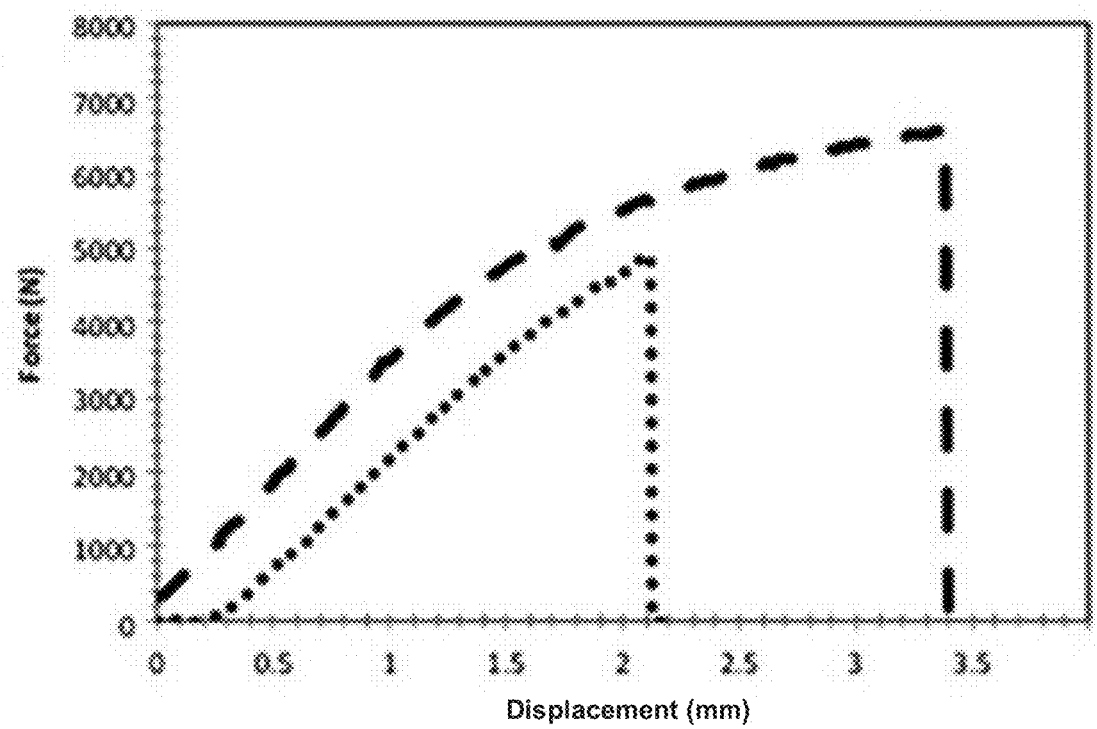
FIG._7A
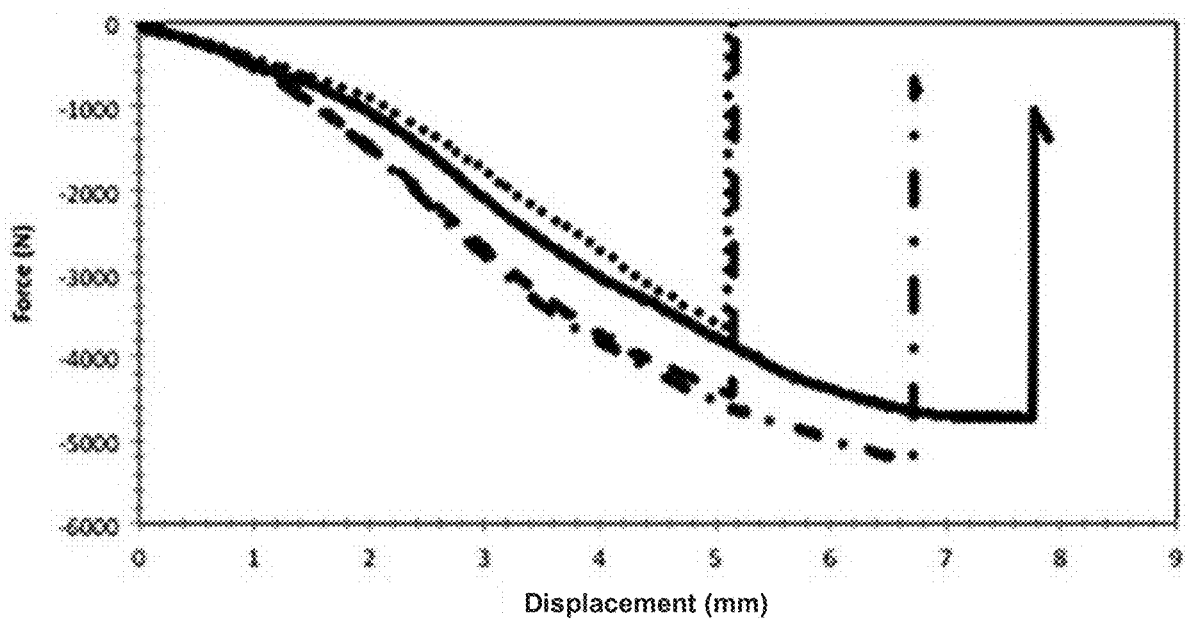
FIG._7B

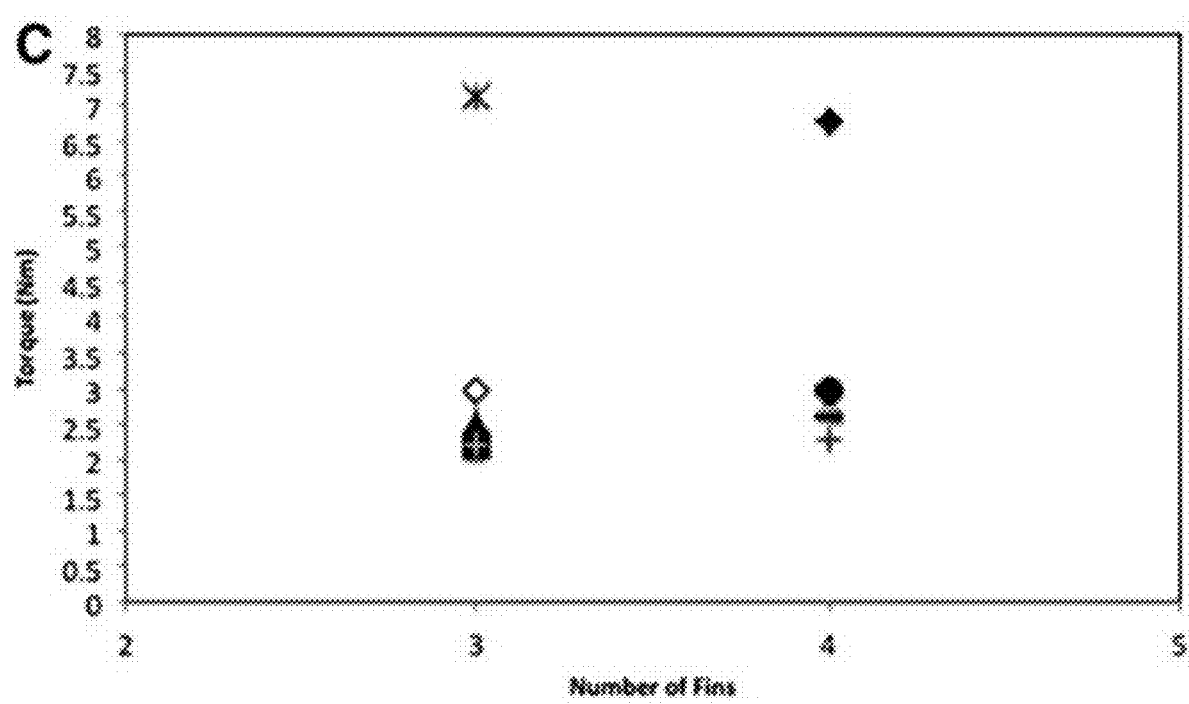
FIG._7C

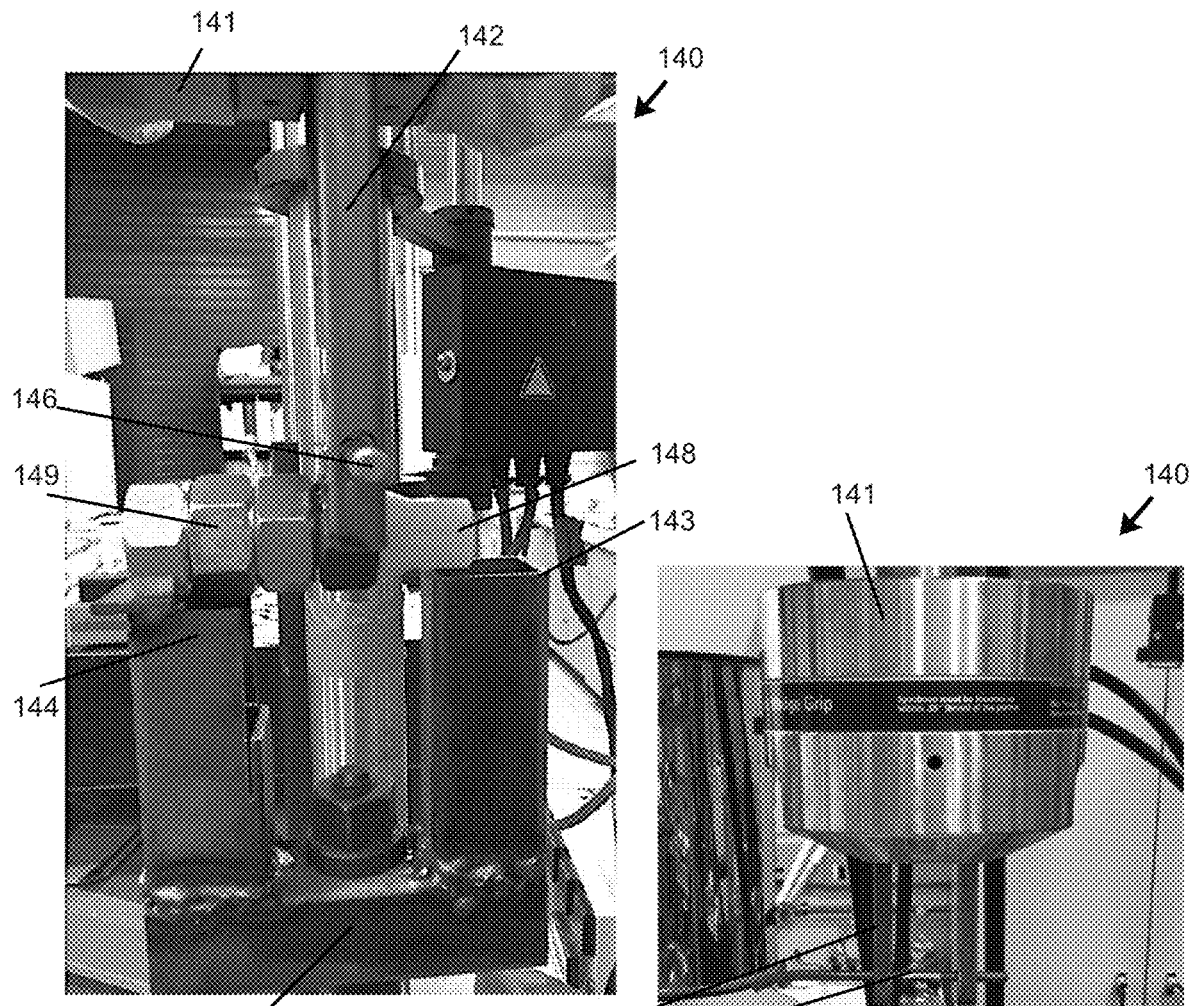
FIG._8A
FIG._8B

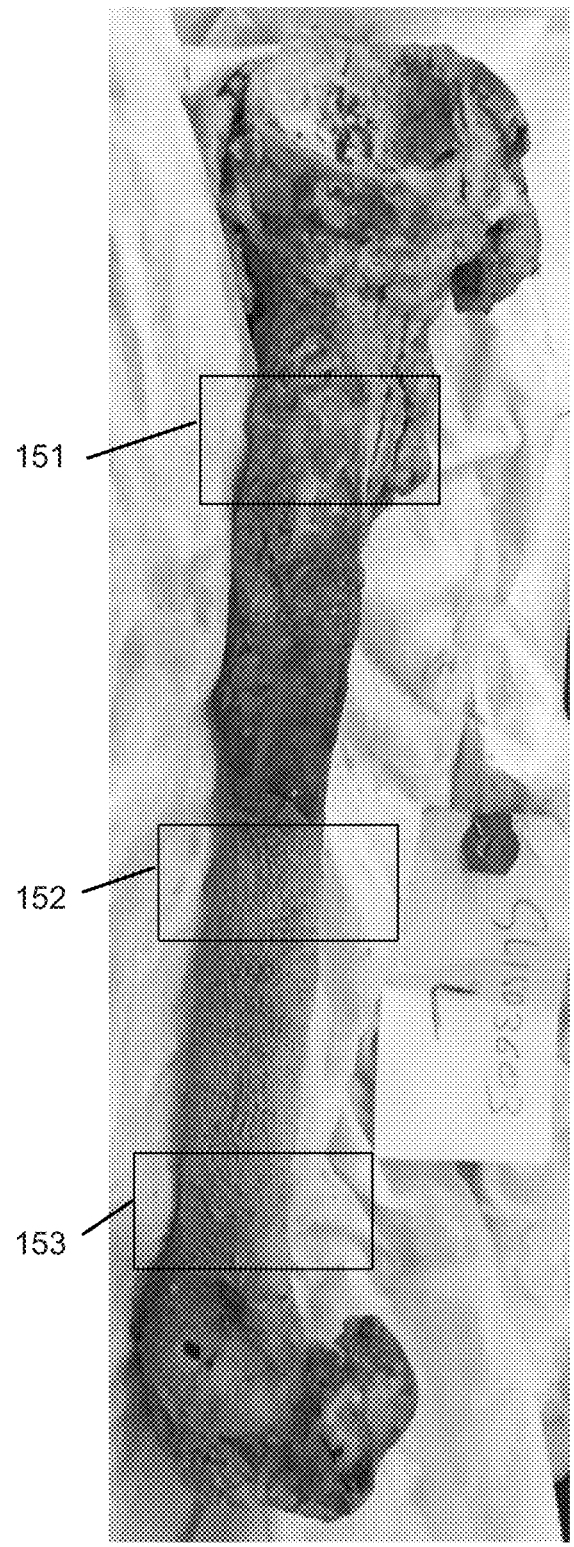
FIG._9A   FIG._9B

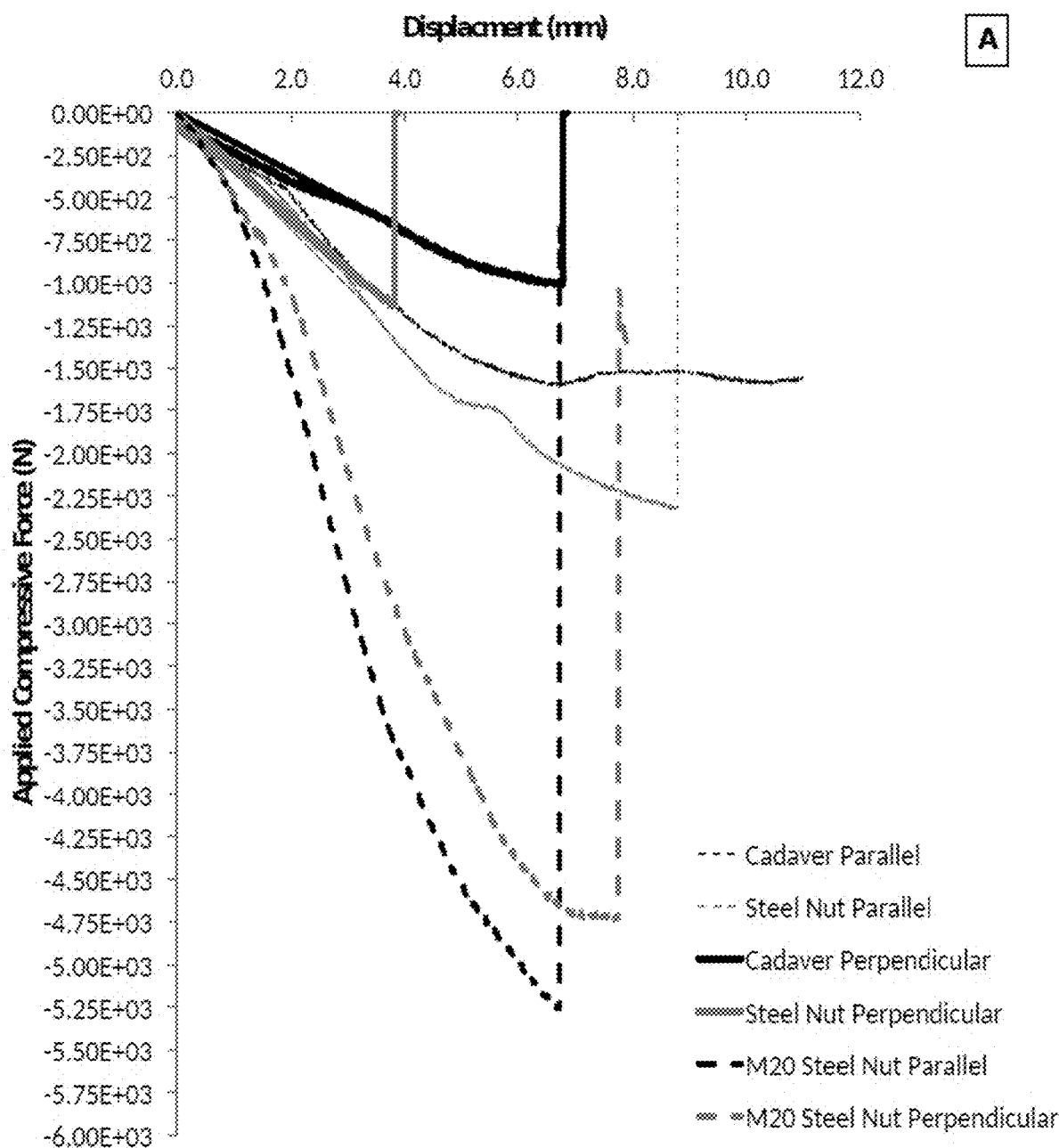
FIG._10A

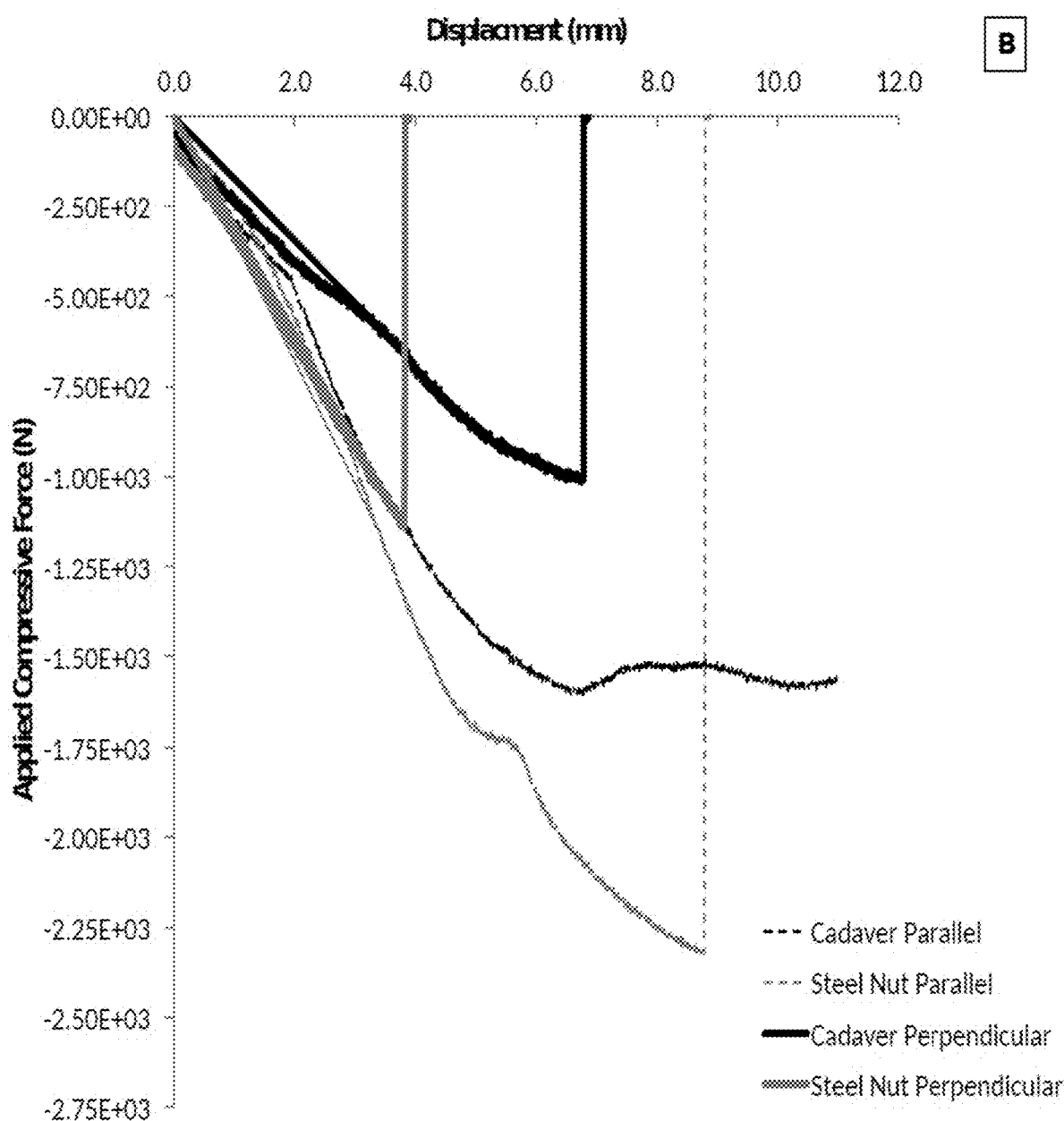
FIG._10B

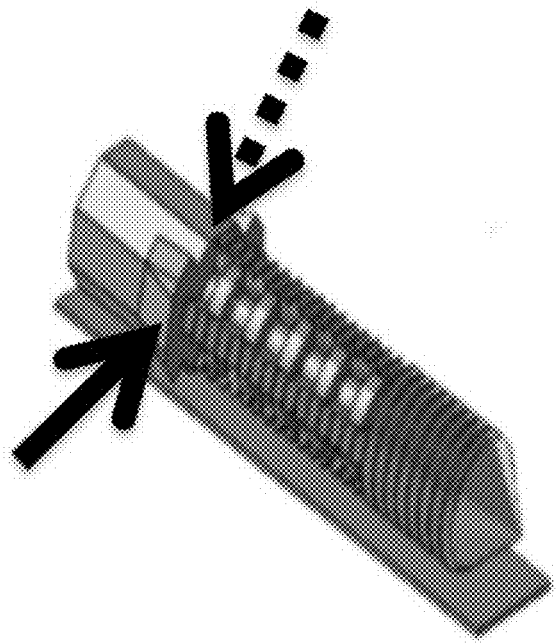
FIG._10C
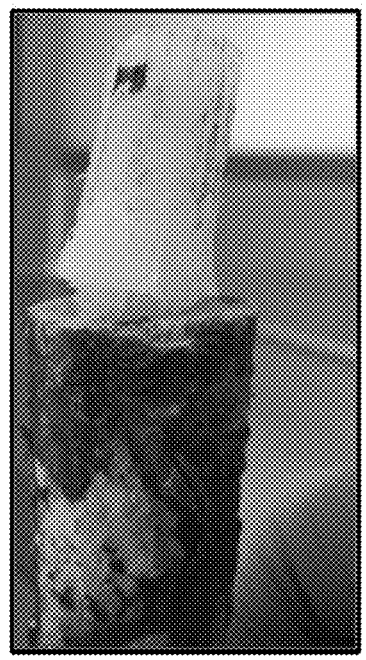
FIG._11A
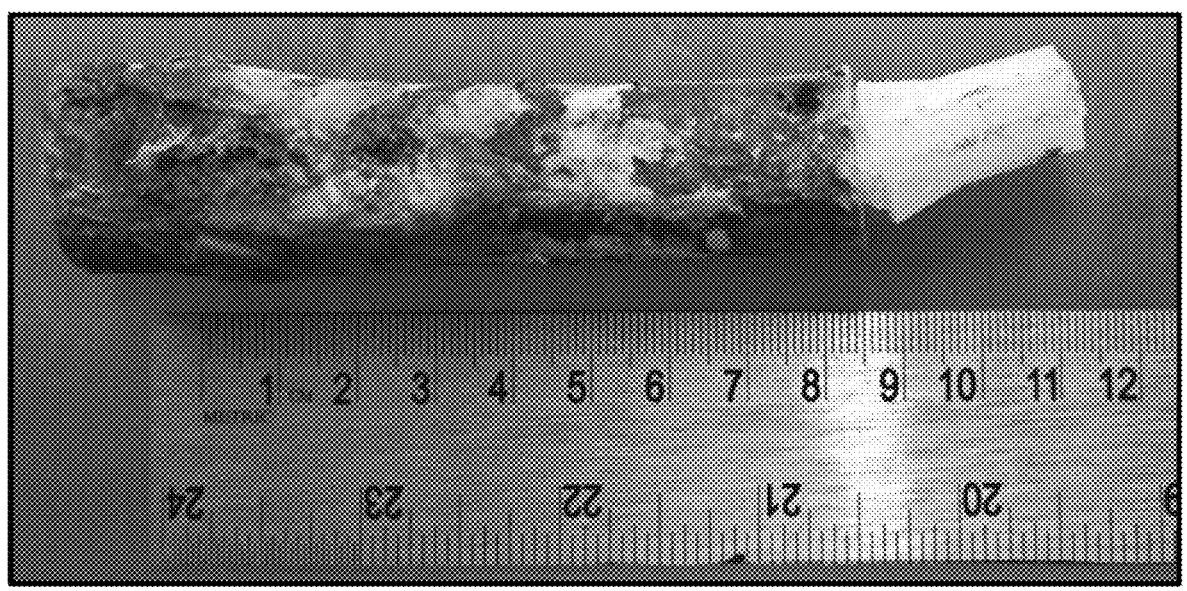
FIG._11B

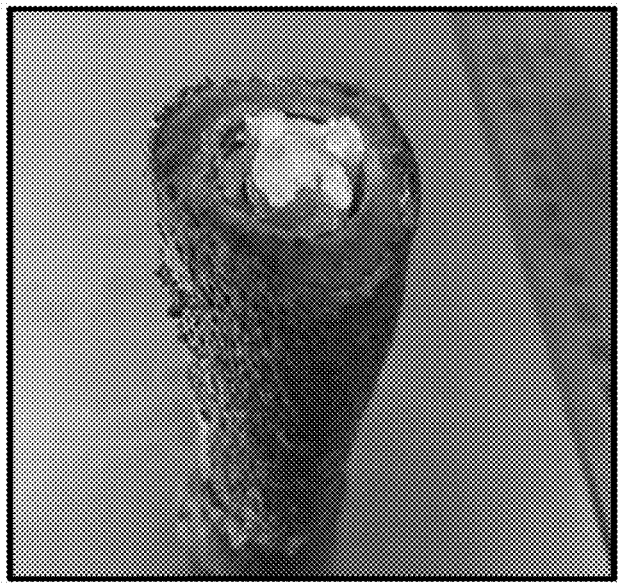
*FIG._11C*
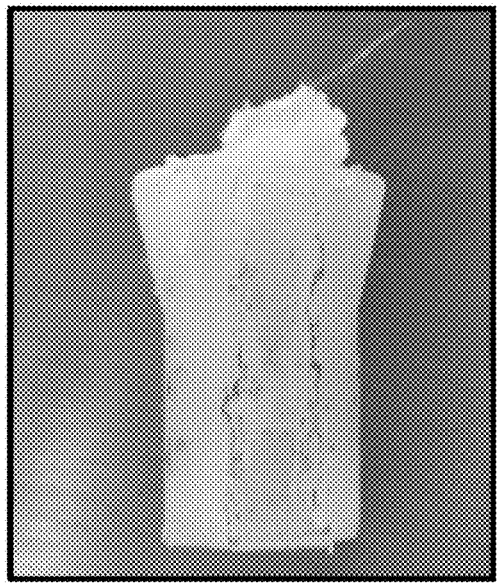
*FIG._11D*
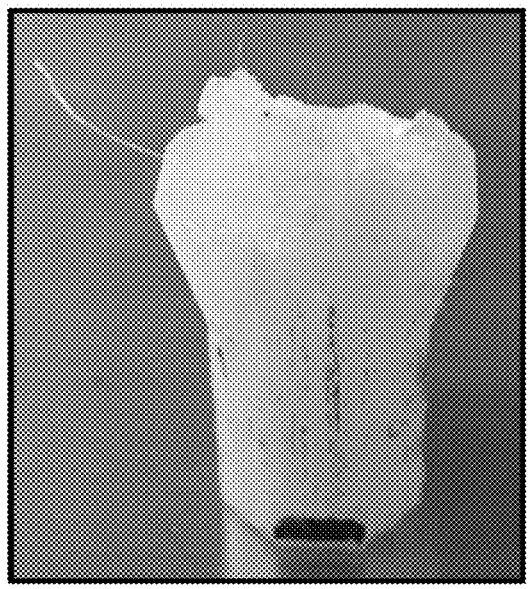
*FIG._11E*

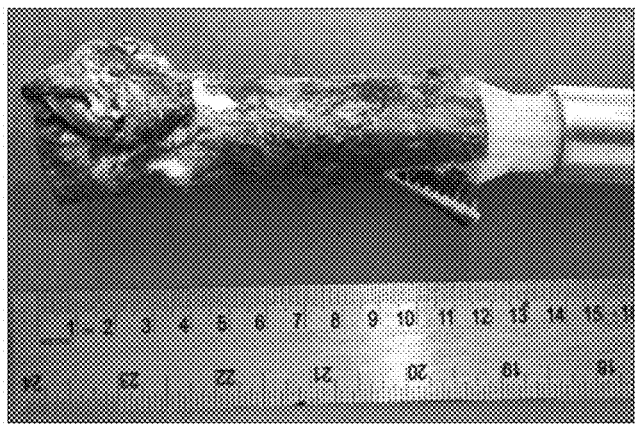
FIG._12B
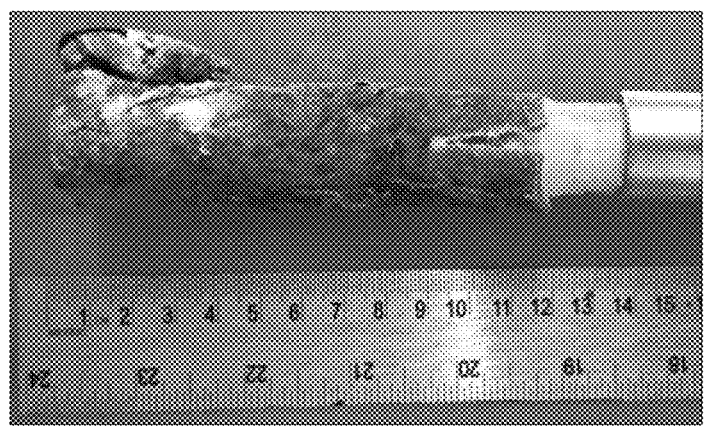
FIG._12C
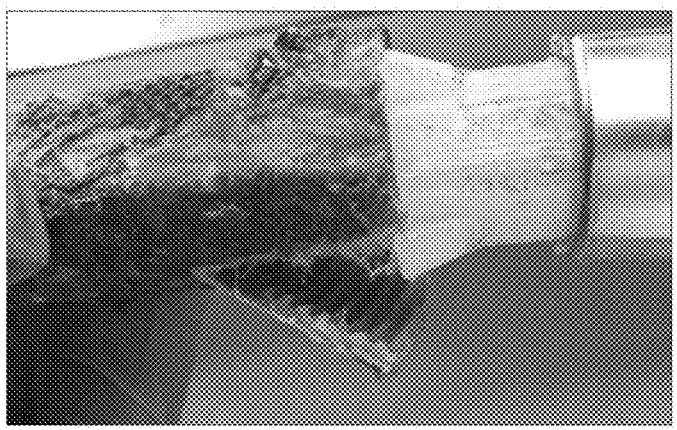
FIG._12D

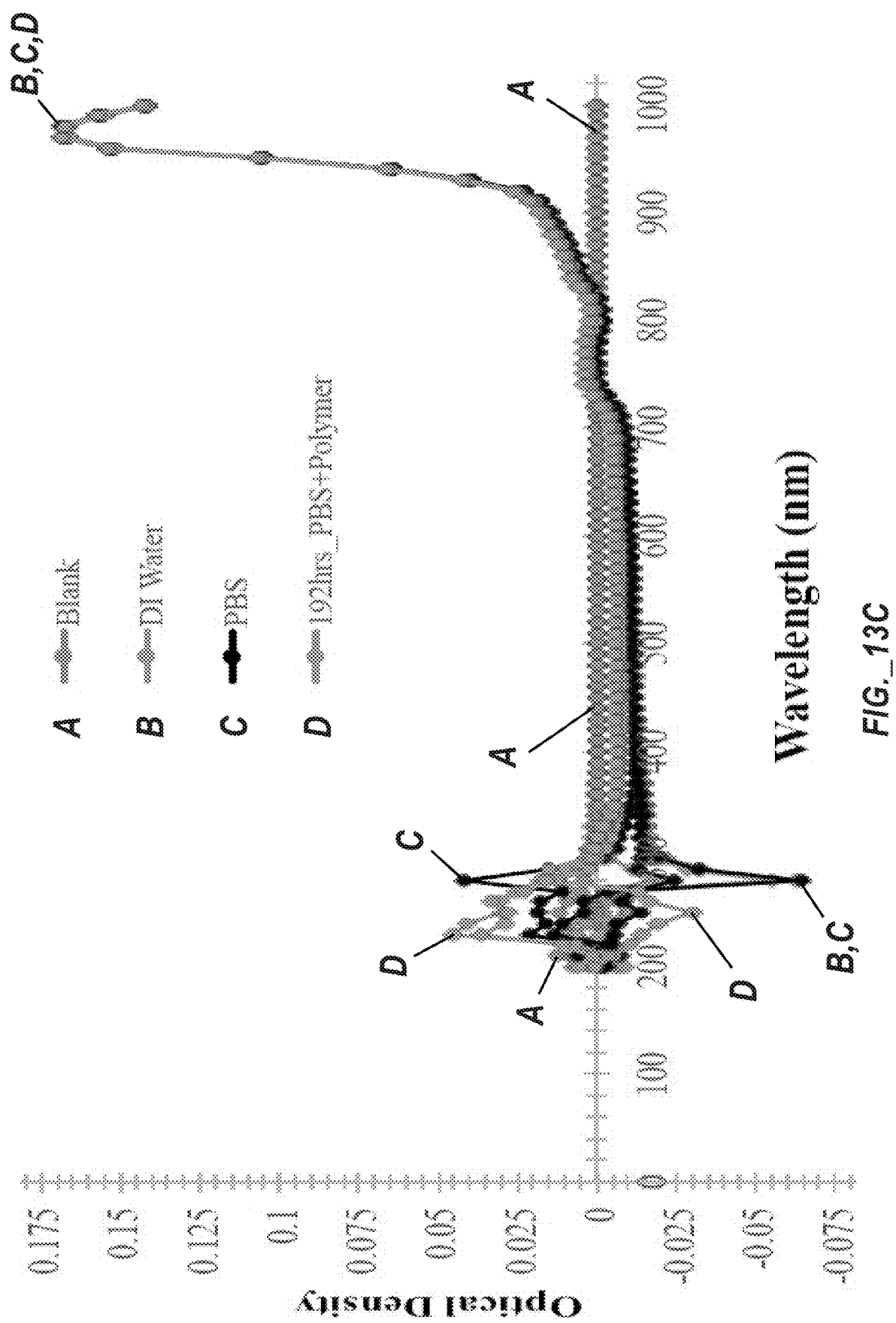
FIG._13C

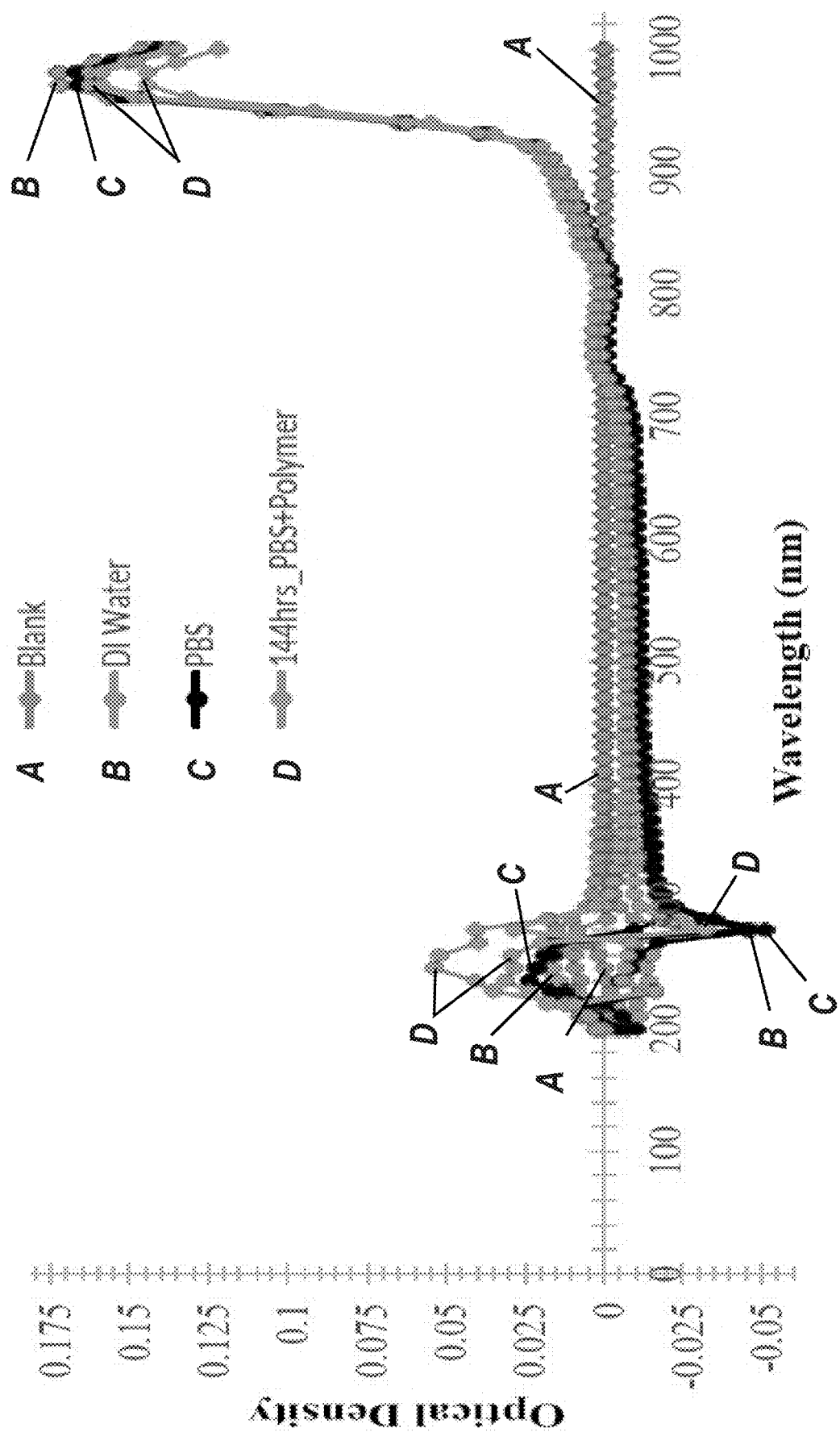
FIG._13D

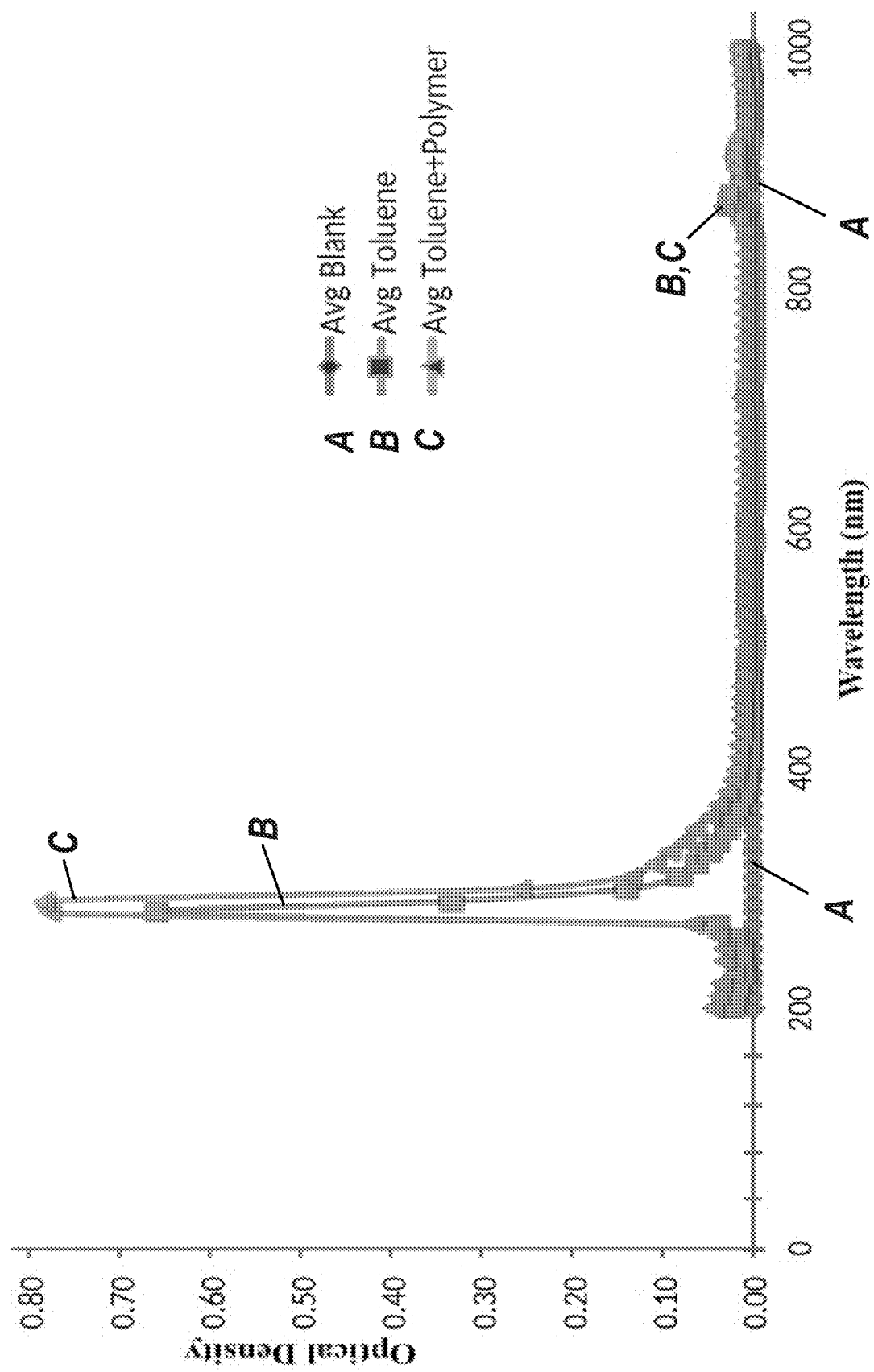
FIG._14B

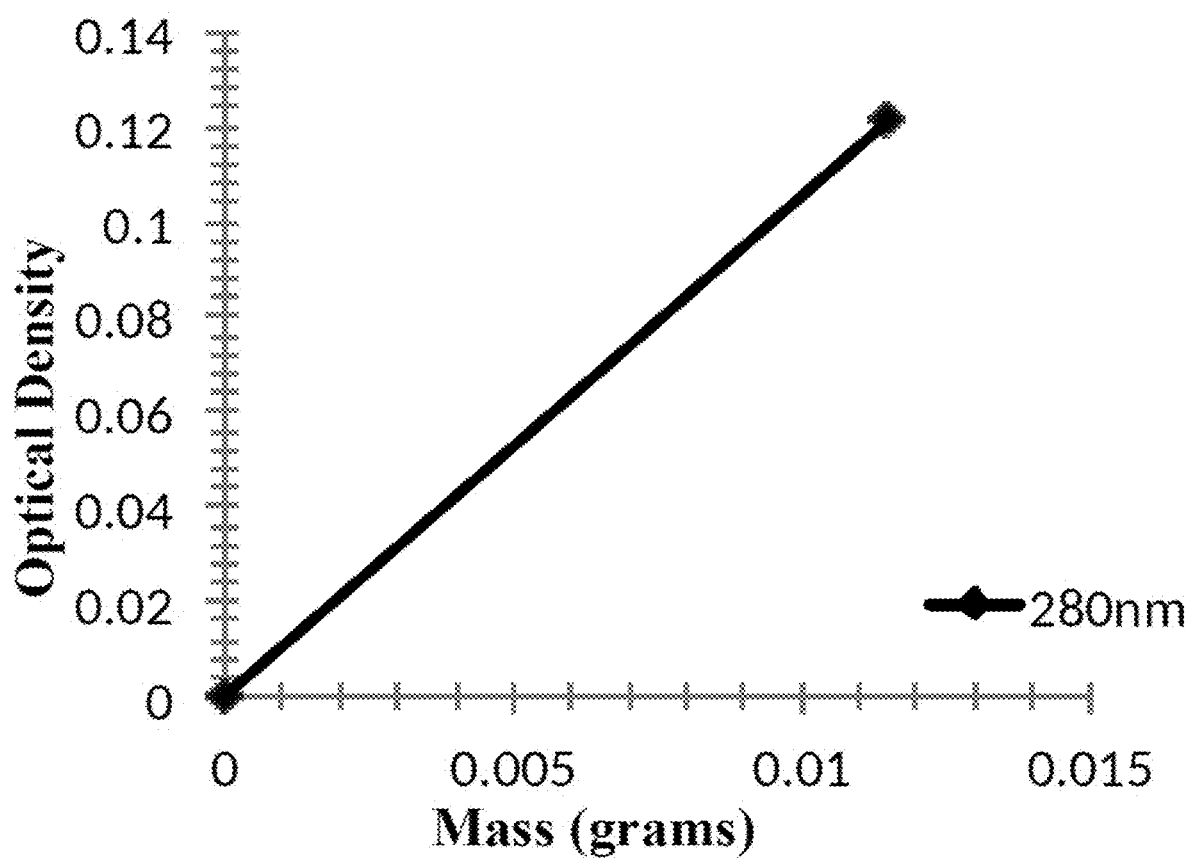
FIG._14C

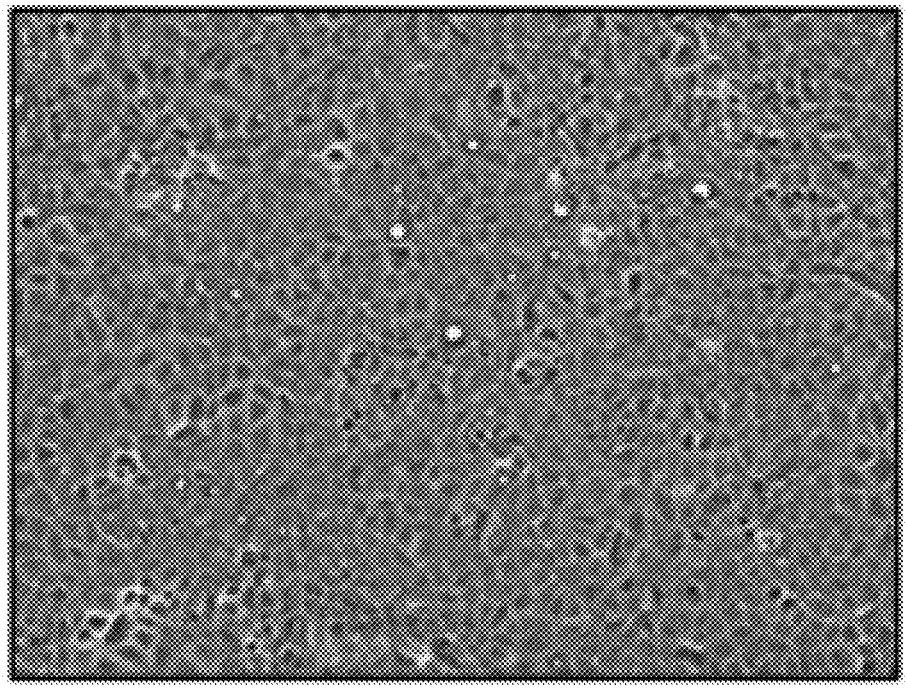
FIG._15A
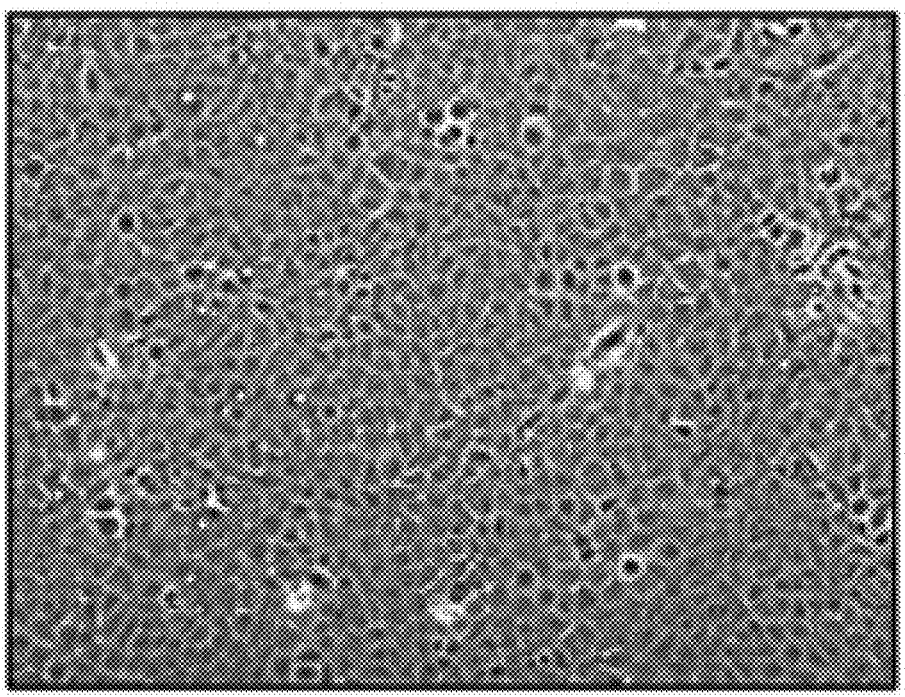
FIG._15B

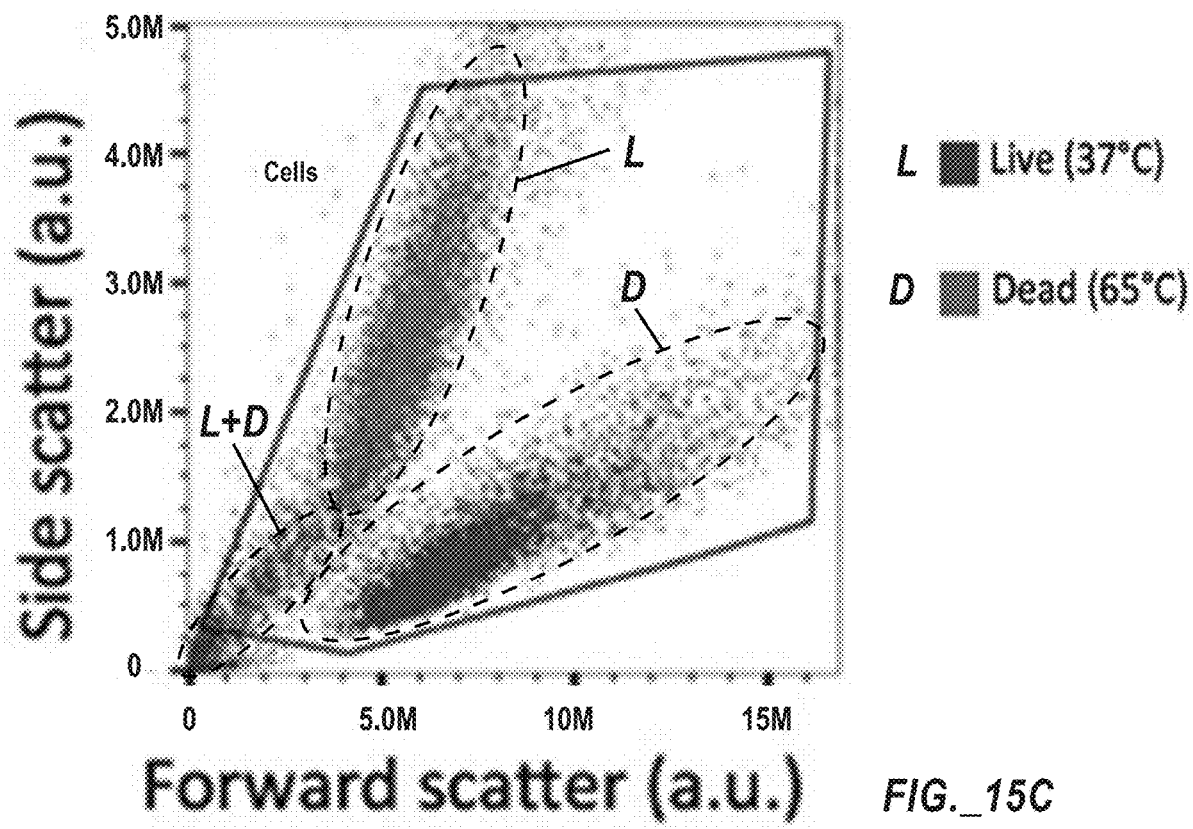
FIG._15C
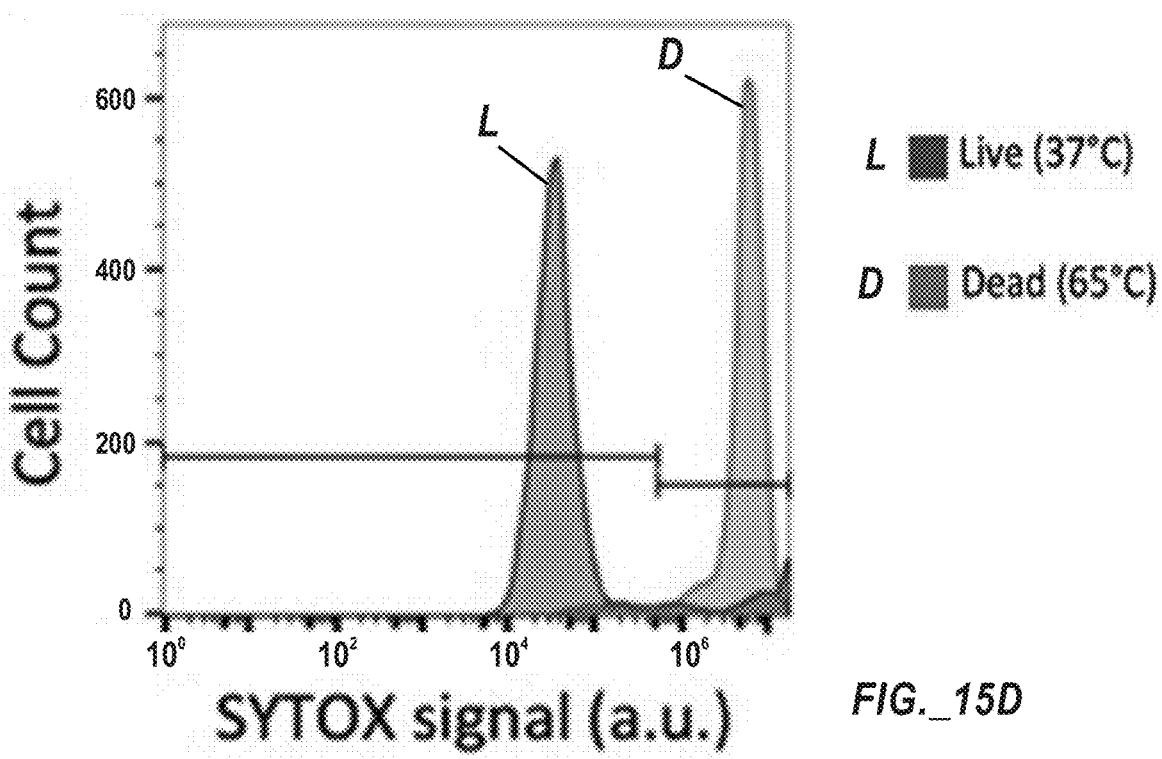
FIG._15D

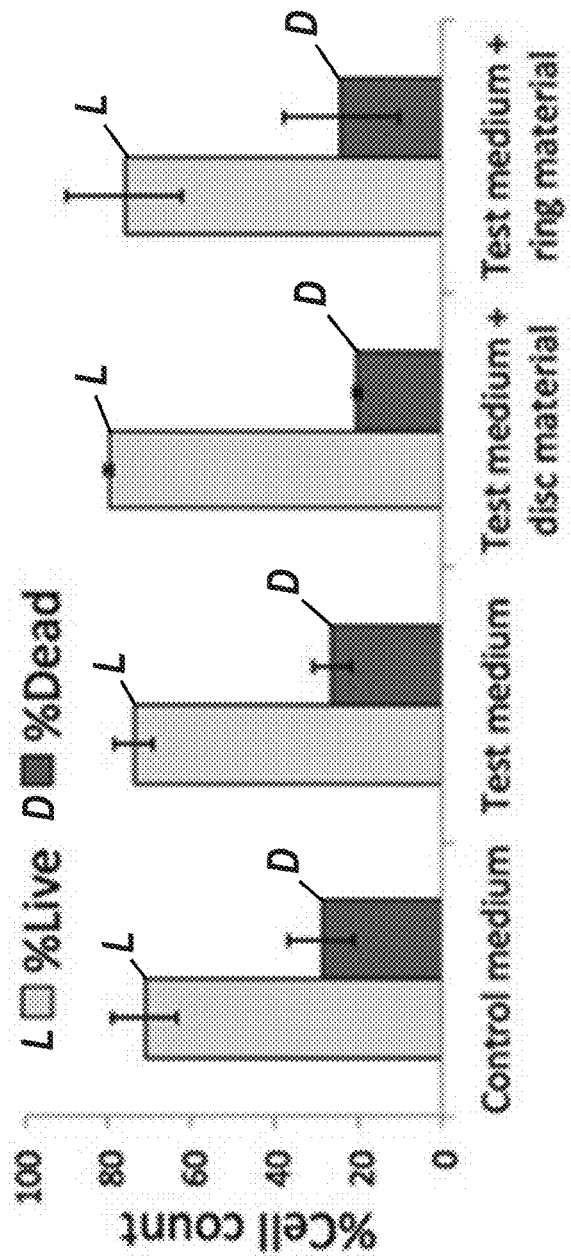
FIG._15E
| Dimensions | Upper (mm) | Middle (mm) | Lower (mm) | Length Between Upper and Lower Region (mm) |
|---|---|---|---|---|
| Sample 1 | 23x24 | 19x21 | 21x23 | 190 |
| Sample 2 | 22x24 | 19x22 | 19x21 | 210 |
| Sample 3 | 28x32 | 22x27 | 22x23 | 240 |
FIG._16

FIG. 17A

|  | M14 × 2.0mm ||||  M20 × 2.5mm ||
|---|---|---|---|---|---|---|
|  | Steel Nut Perpendicular | Steel Nut Parallel | Cadaver Perpendicular | Cadaver Parallel | Steel Nut Parallel | Steel Nut Perpendicular |
| Max Displacement (mm) | 3.8947606 | 8.8763523 | 6.8672595 | 10.988303 | 6.8295454 | 7.89580793 |
| Max Force (kN) | 1.139973 | 2.3259392 | 1.0151346 | 1.6097603 | 5.2596453 | 4.7372942 |

FIG. 17B

| Change from Steel Nut to Cadaver | Perpendicular | | Parallel | |
|---|---|---|---|---|
| Max Displacement Increase % (mm) | 43.28508192 | Increase from Steel to Cadaver | 19.21998966 | Increase from Steel to Cadaver |
| Max Force % (kN) | -12.29771894 | Decrease from Steel to Cadaver | -44.48978522 | Decrease from Steel to Cadaver |
| Change From M14 to M20 | Perpendicular | | Parallel | |
| Max Displacement Increase % (mm) | 50.67305798 | Increase from M14 to M20 | -29.96988496 | Decrease from M14 to M20 |
| Max Force % (kN) | 75.93620004 | Increase from M14 to M20 | 55.77764151 | Increase from M14 to M20 |

OSSEOINTEGRATABLE PROSTHETIC DEVICE AND MANUFACTURING METHOD

STATEMENT OF RELATED APPLICATION(S)

This application claims the benefit of provisional patent application Ser. No. 62/376,184, filed Aug. 17, 2016, the disclosure of which is hereby incorporated by reference herein in its entirety.

TECHNICAL FIELD

This disclosure relates to prosthetic devices that may be integrated with skeletal bones of mammalian users, as well as methods for their manufacture and use.

BACKGROUND

In the United States, about two million people have lost a limb, and about 185,000 people each year lose a limb, with hospital costs for amputations of approximately $8.3 billion each year. 54% of limb losses are attributable to vascular diseases, including diabetes and peripheral arterial disease; about 45% of limb losses are attributable to physical trauma; and fewer than 2% of limb losses are attributable to cancer, with a ratio of upper limb to lower limb loss of 1:4. Prosthetics can cost up to $50,000 per limb, and a significant number (possibly a majority) are not covered by insurance. Additionally, many prosthetics need to be replaced as the user grows, and health insurance frequently does not cover the cost of continual replacement.

One desirable focus of this disclosure will be on upper limb prosthetics and specifically trans-humeral limb amputations. Currently, upper limb prosthetics can weigh up to eight pounds, and transhumeral prosthetics can sometimes weigh even more. These types of prosthetics are attached to the user either by a socket and sleeve system or with an osseointegrated prosthesis, which allows an abutment or shaft to attach directly to the skeletal bone system and protrude from the user's skin for attachment of a prosthetic limb.

Prosthetics are commonly attached to the user with a socket and sleeve system due to its lower costs, degree of formability to the amputated limb, and easiness of implementation for the wearer. The pitfalls of a socket and sleeve system are user discomfort due to changes in stump shape throughout the day caused by swelling, the socket shifting during use, and sweat pooling due to little or no airflow throughout the socket for heat exchange.

Socket and sleeve systems also have weak attachment strengths when compared to osseointegrated systems, since the socket and sleeve are only attached to the user's skin. Such prosthetics can "wobble," or have "play," since they are only attached to the skin, thereby allowing for movement of the prosthetics caused by the skin moving relative to the muscle, and the muscle moving relative to the bone. Additionally, socket and sleeve systems cause a loss of sensation for the user because the socket creates a barrier between the prosthetic and the user's skin, which does not allow forces or vibrations to be transferred to the user directly.

To overcome disadvantages associated with socket and sleeve systems, osseointegrated prosthetic devices providing direct attachment to skeletal bone may be used. Such devices allow for forces and vibrations to be sensed by the user's nervous system through the user's skeletal structure, and help reduce or sometimes eliminate the pain associated with phantom limb.

Different types of osseointegrated prosthetics include: (i) cylindrical/coned rods that are press fitted into the bone cannel; (ii) an "x-shape" rod that allows bone tissue ingrowth into the voided space, and (iii) two-part systems that are composed of a sleeve and an abutment that protrudes out of the skin. In the latter type, the abutment either attaches with a tapered press fit or has threads to engage with the sleeve, with threaded sleeves and abutment/screws being the most preferred attachment system. FIG. 1 shows a representative two-part osseointegrated screw system 10 implanted into a limb that includes soft tissue 12 surrounding a bone 16, with the osseointegrated screw system 10 including a fixture/sleeve 18 and an abutment 20, with the fixture/sleeve 18 including outer threads to create fixation to the bone 16 and inner threads to receive the abutment 20, and with a shaft 22 extending through the soft tissue 12 and skin 14 covering the limb. The two-part osseointegrated screw system 10 allows the bone 16 to grow around and into the outer threads of a porous surface coating of the fixture/sleeve 18 to create a hard fixation point, and then uses the abutment 20 to enable attachment of an external prosthetic limb. The two-part osseointegrated screw system 10 is inserted in two separate surgeries, including a first surgery to insert the fixture/sleeve 18 (which requires six months of recovery) followed by a second surgery to insert the abutment 20 (which requires 12-16 months of recovery/rehabilitation to be able to put full force on the system).

Conventional osseointegrated prosthetics are made of titanium due to its biocompatibility and high strength. The two-part osseointegrated screw systems described hereinabove have long surgical recovery times and the titanium used in construction has a dramatically higher elastic modulus (around 120 GPa) than cortical bone (having an elastic modulus of around 12-16 GPa). This difference in elastic modulus causes stress shielding to the bone. Such stress shielding causes the skeletal bone cells to pull away from the site of fixation since the bone cells do not receive any forces that would require bone cell formation, thereby leading to loosening of the prosthetic attachment system. Additionally, conventional current osseointegrated screws do not allow for large amounts of bone ingrowth, cannot be quickly or easily manufactured to match the anatomical shape/size of the user's skeletal bone shafts, and cannot be implanted via a one-step surgical process.

In consequence of the foregoing considerations, the art continues to seek improved osseointegrated prosthetic systems.

SUMMARY

Disclosed herein are novel osseointegratable prosthetic devices as well as methods for their manufacture and use. An osseointegratable prosthetic device suitable for implantation via a one-step surgical process includes a threaded insertion end, an externally accessible tool interface end, and an intermediately arranged scaffold portion defining recesses that permit ingrowth of skeletal tissue. Preferably, the osseointegratable prosthetic device embodies a unitary body structure, may be fabricated in various materials (including polymeric materials), and is amenable to various fabrication techniques including fused filament fabrication (FFF, a/k/a fused deposition modeling).

In one aspect, an osseointegratable prosthetic device comprises: a body structure comprising an insertion end and an external interface end; an externally threaded anchor portion proximate to the insertion end; a tool interface portion comprising at least one tool-receiving surface proximate to the external interface end; and a scaffold portion comprising a plurality of recesses configured to permit ingrowth of skeletal tissue, wherein the scaffold portion is arranged between the externally threaded anchor portion and the tool interface portion.

In certain embodiments, the osseointegratable prosthetic device further comprises a plurality of longitudinal fins extending between the externally threaded anchor portion and the tool interface portion, wherein the plurality of longitudinal fins comprises externally threaded peripheral surfaces. In certain embodiments, the externally threaded peripheral surfaces of the plurality of longitudinal fins follow the shape and pitch of threads of the externally threaded anchor portion. In certain embodiments, the plurality of longitudinal fins includes at least three, at least four, or more longitudinal fins. In certain embodiments, the osseointegratable prosthetic device further comprises a plurality of apertures defined in the plurality of longitudinal fins, such as may be useful to facilitate ingrowth of skeletal tissue and/or passage of fluid.

In certain embodiments, the body structure comprises a longitudinal core extending between the externally threaded anchor portion and the tool interface portion, and the osseointegratable prosthetic device further includes a plurality of transverse ribs extending radially outward from the longitudinal core. In certain embodiments, the plurality of transverse ribs is provided in addition to, and extending perpendicular to, the plurality of longitudinal fins.

In certain embodiments, the osseointegratable prosthetic device further comprises a flange portion arranged between the tool interface portion and the scaffold portion, wherein the flange portion comprises a maximum transverse dimension that exceeds a maximum transverse dimension of the scaffold portion. In certain embodiments, the flange portion comprises a first radially extending flange element, and a second radially extending flange element that is discontinuous relative to the first radially extending flange element.

In certain embodiments, the body structure comprises a polymeric material. In certain embodiments, the body structure comprises a thermoplastic material. In certain embodiments, the body structure comprises a polyamide material. In certain embodiments, the body structure embodies a unitary, fused polymeric body structure. In other embodiments, the body structure may comprise one or more metals.

In certain embodiments, at least some recesses of the plurality of recesses contain porous material. In certain embodiments, at least some recesses of the plurality of recesses contain organic material. In certain embodiments, at least some recesses of the plurality of recesses contain cellular material.

In another aspect, the disclosure relates to a method of fabricating the osseointegratable prosthetic device as described herein, the method comprising: heating a thermoplastic material to a flowable state; and selectively depositing the heated thermoplastic material in sequential layers to form the body structure including the externally threaded anchor portion, the tool interface portion, and the scaffold portion; wherein the body structure embodies a unitary, fused polymeric body structure.

In certain embodiments, prior to the heating, the thermoplastic material comprises a thermoplastic filament. In certain embodiments, the method further comprises supplying at least one material to at least some recesses of the plurality of recesses, wherein the at least one material comprises one or more of a porous material, an organic material, or a cellular material.

In another aspect, the disclosure relates to a method of fabricating the osseointegratable prosthetic device as described herein, the method comprising: selectively depositing at least one layer of structural material; supplying energy to the at least one layer of structural material to fuse the at least one layer of structural material to an underlying layer of structural material; and repeating the selective deposition and energy supplying steps to form the body structure including the externally threaded anchor portion, the tool interface portion, and the scaffold portion.

In certain embodiments, the at least one layer of structural material comprises a resin, and the energy supplying step comprises impinging photonic energy on the at least one layer of structural material. In certain embodiments, the at least one layer of structural material comprises a powder (e.g., a metal and/or a polymeric material), and the energy supplying step comprises impinging laser emissions on the at least one layer of structural material. In certain embodiments, the method further comprises supplying at least one material to at least some recesses of the plurality of recesses, wherein the at least one material comprises one or more of a porous material, an organic material, or a cellular material.

In another aspect, the disclosure relates to a method for facilitating attachment of a prosthetic limb to a mammalian user, the method comprising: defining a cavity in a bone of the mammalian user, and threading the osseointegratable prosthetic device as described herein into the cavity.

In another aspect, any one or more aspects or features described herein may be combined with any one or more other aspects or features for additional advantage.

BRIEF DESCRIPTION OF THE DRAWINGS

FIG. 1 is a schematic of transhumeral amputation with a conventional two-part osseointegrated screw system (prosthetic implant).

FIG. 2 is a table identifying repeating units for certain aliphatic polyamides.

FIG. 3B is a plot of tensile stress peak force (GPa) versus dog bone percent infill for the dog bone shaped test sample of FIG. 3A.

FIG. 3C is a perspective view of the dog bone shaped test sample of FIGS. 3A and 3B.

FIG. 3E is a plot of peak shear force (kN) as a function of 3D printer layer height (mm), with a shaded region representing the increase in moment arm and cross-sectional area (legend: circle is 0.10 mm, cross is 0.15 mm, triangle is 0.20 mm, square is 0.25 mm, and diamond is 0.30 mm).

FIG. 3F is a side elevation view of a fused filament fabrication 3D printed shear test sample, with the printing direction indicated by the bold arrow (the bottom of the arrow being closer to the platform of the 3D printer and the top arrow indicating the nozzle direction in the z-axis).

FIG. 3G is a perspective view of the fused filament fabrication 3D printed shear test sample of FIG. 3F.

FIG. 4A is a perspective view of a solid model of a scaffold portion of an osseointegratable prosthetic device, with the scaffold portion including fins but being devoid of a longitudinal core (or center rod) having a width greater than that of the fins.

FIG. 4B is a perspective view of a solid model of a scaffold portion of an osseointegratable prosthetic device, with the scaffold portion including fins and a cylinder-shaped longitudinal core (or center rod).

FIG. 4C is a perspective view of a solid model of a scaffold portion of an osseointegratable prosthetic device, with the scaffold portion including fins, a cylinder-shaped longitudinal core (or center rod), and multiple transverse ribs.

FIG. 4D is a perspective view of a solid model of a scaffold portion of an osseointegratable prosthetic device, with the scaffold portion including a cylinder-shaped longitudinal core (or center rod) and a helix-shaped rib structure (or helical ribs) surrounding the core.

FIG. 4E is a top plan view of the solid model of the scaffold portion of the osseointegratable prosthetic device of FIG. 4D.

FIG. 4F is a table of finite element modeling simulation results including values for change in stress and change in displacement for solid finite element modeling (FEM) performed on the scaffold portions shown in FIGS. 4A-4D.

FIG. 5A is a perspective view illustration of a fused filament fabrication 3D printed osseointegratable prosthetic device including a scaffold portion with three longitudinal fins and multiple annular shaped transverse ribs according to one embodiment.

FIG. 5B is a table providing area, volume, and dimension data for the fused filament fabrication 3D printed osseointegratable prosthetic device of FIG. 5A.

FIG. 6A is a side elevation view illustration of a fused filament fabrication 3D printed osseointegratable prosthetic device including a scaffold portion with four longitudinal fins and multiple annular shaped transverse ribs according to another embodiment.

FIG. 6B is a perspective view illustration of the fused filament fabrication 3D printed osseointegratable prosthetic device of FIG. 6A.

FIG. 6C is a table providing area, volume, and dimension data for the fused filament fabrication 3D printed osseointegratable prosthetic device of FIGS. 6A and 6B.

FIG. 7A provides plots of tension force versus displacement for the fused filament fabrication 3D printed osseointegratable prosthetic devices of FIG. 5A (dotted line) and of FIGS. 6A and 6B (dash line).

FIG. 7B provides plots of three-point bending force versus displacement for the fused filament fabrication 3D printed osseointegratable prosthetic devices of FIG. 5A (dash line is three-fin parallel, and dotted line is three-fin perpendicular) and of FIGS. 6A and 6B (dash-dot line is four-fin parallel, and solid line is four-fin perpendicular).

FIG. 7C is a plot of seating/loosening torques (Nm), and torque-to-failure test results for the fused filament fabrication 3D printed osseointegratable prosthetic devices of FIGS. 5A, 6A, and 6B, wherein the triangle and circle are seating torques, the filled star and diamond are failure torques, and all others are loosening torques.

FIG. 8A is a front view photograph of a three-point bending test fixture for testing a fused filament fabrication 3D printed part.

FIG. 8B is a side view photograph of the three-point bending test fixture of FIG. 8A.

FIG. 9A is a first photograph of a humeral sample obtained from a cadaver to enable testing of 3D printed osseointegratable screw prototypes according to one embodiment of the present disclosure.

FIG. 9B is a second photograph of the humeral sample of FIG. 9A, with addition of rectangles identifying upper, middle, and lower regions of the sample.

FIG. 10A is a plot of displacement versus applied compressive force for three-point bending of M14 and M20 3D printed osseointegratable screws according to the present disclosure threaded into cadaver humeral samples, as well as simulated data for M14 3D printed osseointegratable screws threaded into steel nuts, with the applied force perpendicular and parallel to the partial flange design.

FIG. 10B represents a subset of data plotted in FIG. 10A, embodying a plot of displacement versus applied compressive force for three-point bending of M14 3D printed osseointegratable screws threaded into cadaver humeral samples, as well as the simulated data for M14 3D printed osseointegratable screws threaded into steel nuts.

FIG. 10C is a perspective view of a 3D printed osseointegratable screw according to one embodiment, with a solid arrow showing a direction of applied bending force extending parallel to first and second radially extending flange elements of the osseointegratable screw (thereby representing an increased cross-sectional area), and with a dashed arrow showing a direction of applied bending force extending perpendicular to the first and second radially extending flange elements (thereby representing a reduced cross-sectional area).

FIG. 11A is a side elevation view photograph of a portion of a M14 3D printed osseointegratable screw threaded into a cadaver humeral sample, following three-point bending failure, with the applied bending force extending parallel to first and second radially extending flange elements of the osseointegratable screw.

FIG. 11B is a magnified front elevation view photograph of the osseointegratable screw and cadaver humeral sample of FIG. 11A, with the photograph further including a ruler to provide an indication of length of the cadaver humeral sample and a head portion of the osseointegratable screw.

FIG. 11C is a perspective view photograph of a central (e.g., scaffold) portion of the osseointegratable screw retained in the cadaver humeral sample of FIGS. 11A and 11B following three-point bending failure, with the applied bending force extending perpendicular to first and second radially extending flange elements of the osseointegratable screw.

FIG. 11D is a side elevation view photograph of a tool interface portion of the osseointegratable screw of FIG. 11C following bending failure and removal from the central (scaffold) portion.

FIG. 11E is a front elevation view photograph of the tool interface portion of FIG. 11D.

FIGS. 12B-12D are side view photographs of a 3D printed osseointegratable screw threaded into a cadaver humeral sample following torque insertion failure, resulting in fracture of the cadaver humeral sample.

FIG. 13C is a plot of optical density versus wavelength (nm) for a polymer leaching study conducted with polyamide six 3D printed material in a phosphate buffer solution for incubation at 192 hours with a sample size of N=3.

FIG. 13D is a plot of optical density versus wavelength (nm) for a polymer leaching study conducted with polyamide six 3D printed material in a phosphate buffer solution for incubation at 144 hours with a sample size of N=3.

FIG. 14B is a plot of optical density versus wavelength (nm) for dissolved polymer powder in toluene versus neat toluene to determine the impact of chemical leaching into the solution.

FIG. 14C is a plot of optical density versus mass for 11.5 mg of powdered polymer dissolved in toluene at 280 nm wavelength.

FIG. 15A is a phase contrast image (100× magnification) of live U-2 OA cells after 48 hours of growth in a standard medium.

FIG. 15B is a phase contrast image (100× magnification) of live U-2 OA cells after 48 hours of growth in a test medium prepared for determining cytotoxicity of compounds leached from the polyamide six-based material used for fabricating 3D osseointegratable screws according to various experiments.

FIG. 15C is a scatter plot showing forward scatter versus side scatter for flow cytometry analysis of U-2 OA control cells or cells killed with a high-temperature incubation, utilizing ~10,000 cells per sample, and excluding non-cellular particles.

FIG. 15D provides superimposed histograms showing average proportions of U-2 OA live and dead cells determined by the SYTOX® signal threshold for the control cells or cells killed with high-temperature incubation according to FIG. 15C.

FIG. 15E is a bar chart showing average proportions for U-2 OA live and dead cells (~5,000 per sample) determined by the SYTOX® signal threshold (with bar gates) for cells in control medium, in test medium, in test medium plus disc material, and in test medium plus ring material.

FIG. 16 is a table providing dimensions for the upper, middle, and lower regions of the cadaver humeral sample shown in FIG. 9B.

FIG. 17A is a table providing maximum displacement and force values for M14 and M20 3D printed osseointegratable screws threaded into cadaver humeral samples.

FIG. 17B is a table identifying differences between M14 and M20 3D printed osseointegratable screws threaded into cadaver humeral samples to M14 and M20 3D printed osseointegratable screws threaded into simulated steel nuts.

DETAILED DESCRIPTION

Figure 3A:
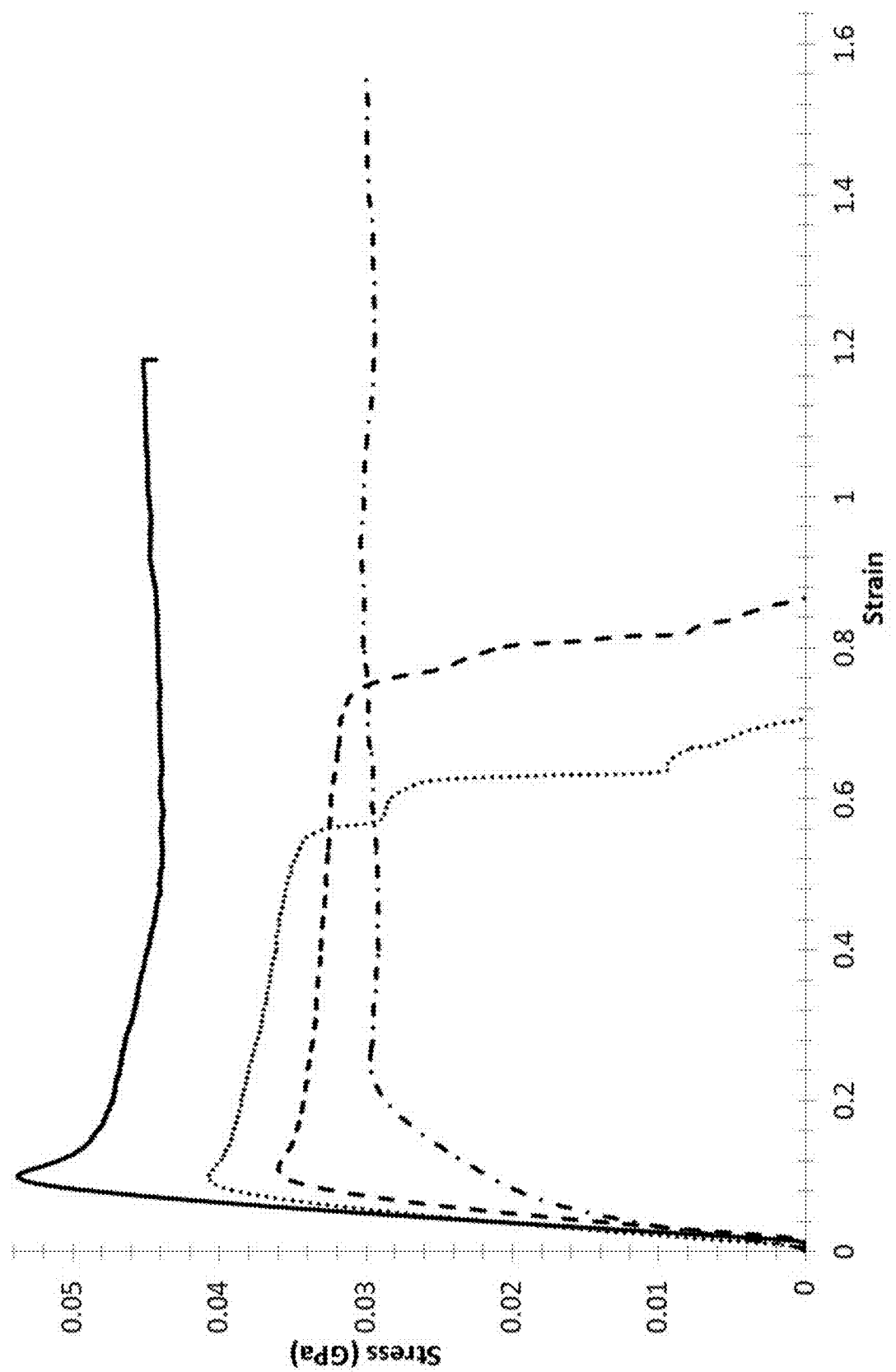
FIG. 3A is a plot of stress (GPa) versus strain for a tensile test of a fused filament fabrication 3D printed dog bone shaped test sample (the solid line is 100%, the dotted line is 70%, the dash line is 40%, and the dash dot line is 10% infill).

Disclosed herein are novel osseointegratable prosthetic devices as well as methods for their manufacture and use. An osseointegratable prosthetic device suitable for implantation via a one-step surgical process includes a threaded insertion end, an externally accessible tool interface end, and an intermediately arranged scaffold portion defining recesses that permit ingrowth of skeletal tissue. Preferably, the osseointegratable prosthetic device embodies a unitary body structure, may be fabricated in various materials (including polymeric materials), and is amenable to various fabrication techniques including fused filament fabrication (FFF, also known as fused deposition modeling).

The design is an improvement upon conventional two-part osseointegrated prosthetics that are composed of a fixture and abutment. Such conventional prosthetics require two invasive surgeries for implantation (with attendant recovery times for each surgery) and are made of titanium, which has an elastic modulus greater than bone. An elastic modulus greater than bone causes stress shielding and over time can cause loosening of the prosthetic.

Disclosed herein is an alternative to current titanium osseointegrated prosthetics with a thermoplastic FFF 3D printed osseointegratable prosthetic device that can withstand forces greater than an average human humerus bone. The osseointegratable prosthetic device is implantable via a one-step surgical procedure and provides large volumes to enable skeletal bone ingrowth, thereby allowing for an increase in fixation strength.

The osseointegratable prosthetic device design enabling one-step surgical implantation will allow for a significant decrease in rehabilitation time since a patient need not endure two surgeries, as required for implantation of a conventional two-part osseointegration system. It is anticipated that rehabilitation time may be decreased by six months due to the one-step surgical design; however, an animal study is needed to confirm the actual reduction in rehabilitation time. Provision of a flange portion will allow for pretension of the osseointegratable prosthetic device for fitting and rehabilitation. An osseointegratable prosthetic device disclosed herein can also be customized to a specific patient's body with an FFF 3D printer for a point-of-care medical device.

In addition, the osseointegratable prosthetic devices presented herein are anticipated to entail a dramatically lower manufacturing cost than conventional titanium-based designs. Although 3D printer material and medical grade titanium material may be approximately equal in cost per kilogram, cost reductions are implicated in manufacturing and processing, as well as the density difference between the respective materials. A 3D printed osseointegratable prosthetic device according to certain embodiments may be produced in a single production step, whereas the titanium based screws require multiple processing and finishing steps to create the final product. Additionally, the density of medical grade titanium is approximately four times greater than polyamide six-based filament. This allows the polymeric 3D printer filament to have four times the volume of material at the same cost compared to titanium.

Certain embodiments provide a thermoplastic FFF 3D printed osseointegrated upper limb prosthesis for average adult transhumeral amputation, with mechanical properties greater than upper limb skeletal bone. The prosthesis is designed for one-step surgical process, includes a central scaffold portion with large recesses for bone tissue ingrowth for greater stability, and comprises a polyamide six-based material that has an elastic modulus less than skeletal bone, and can be 3D printed for user-specific sizes if needed.

The material was first characterized to establish how percent infill and layer height affected the strength of a printed part, with such characterization yielding unique and unexpected results. Tension samples showed a stabilization period before failure, and shear samples had a unique parabola curve instead of a linear trend in data. Mechanical results of a new prosthetic device according to one embodiment included maximum tensile pullout force of 6568.33N and 5256.37N in bending in a simulated implantation environment. A prosthetic according to one embodiment could also be seated or torqued between 0.50 Nm and 4.00 Nm before failure occurred for a tight-fitting prosthetic for attachment. Such work shows that a 3D printed prosthetic attachment device can be made stronger than bone, and that 3D printing is suitable for producing osseointegratable prosthetic devices.

Sample parts were produced using a fused filament fabrication 3D printing process using a MAKERGEAR® M2 printing apparatus (MakerGear, LLC, Beachwood, Ohio, USA), and were tested on an INSTRON® Model 1331 (maximum load cell capability of 10,000 lbs) or Model 4411 (maximum load cell capability of 900 lbs) (Instron Corporation, Canton, Mass., USA). Part designs were created using SOLIDWORKS® 3D CAD software (Dassault Systemes SolidWorks Corporation, Waltham, Mass., USA), and characterized using custom fabricated tensile and three-point bending test fixtures to accommodate the unique prosthetic device design. Prior to printing, polyamide six filament was dried in an oven at 79° C. for 36-48 hours for a 30 gram roll of filament to ensure that all the moisture was removed before printing. Moisture removal is beneficial to prevent voids in the printed structure.

Each sample part (e.g., osseointegratable prosthetic device) was fabricated of a polyamide six-based material commercially available from Taulman 3D (Saint Peters, Minn., USA), such as Taulman 680 FDA 1.75 mm diameter filament with an elastic modulus of 0.197 GPa. The material is an FDA approved material, designed to meet FDA 21CFR177.1500. Materials compliant with part 177 (for food storage and handling), can be sterilized with ethylene oxide or steam/boiling, and have been used for tissue scaffolding and prosthetics. The polyamide six-based material was chosen because these materials have shown positive results for the use of bone tissue regeneration.

Polyamides are polymers that contain repeating amide, —CO—NH—, linkages. The most widely known manufactured polyamides are often called nylons, and these are aliphatic polyamides (as opposed to aromatic polyamides such as KEVLAR®, E. I. du Pont de Nemours and Co., Wilmington, Del., USA). The nomenclature for describing the linear, aliphatic polyamides is based on the number of carbons in the repeating unit. Examples of repeating units for selected aliphatic polyamides are provided in FIG. 2. The polyamides identified in FIG. 2 are mere examples, without necessarily representing an exhaustive list of materials that might be used. Although prototypes described herein and certain embodiments of the present disclosure may be fabricated of a polyamide six-based material, in other embodiments, polyamide eleven-based or polyamide twelve-based materials exhibiting greater cross-linking may be used.

Figure 3D:
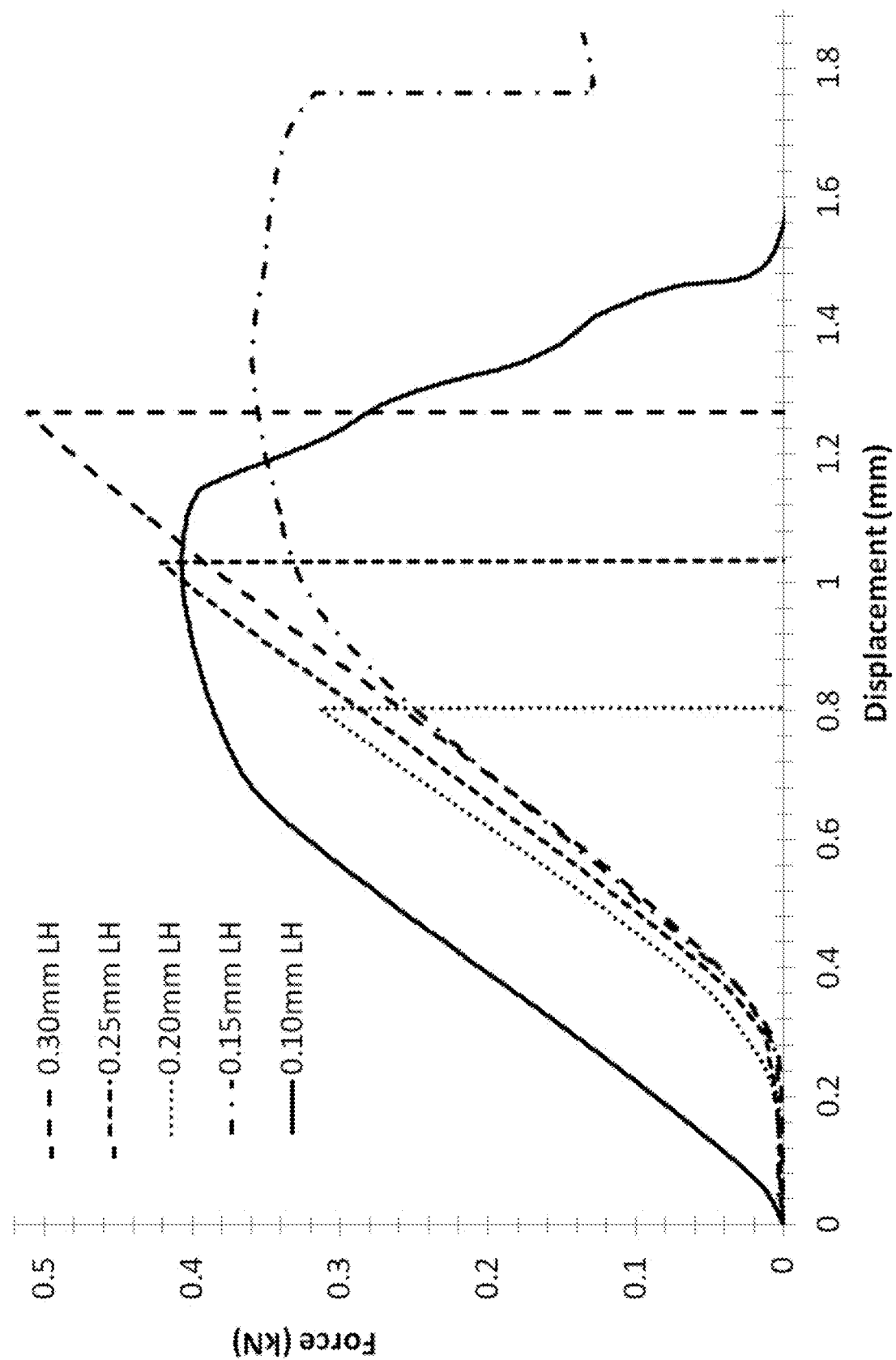
FIG. 3D is a plot of shear force (kN) versus displacement (mm) for a shear test of a fused filament fabrication 3D printed sample.

To determine optimal print settings, tensile testing and shear testing were performed with various parameters, with a sample size of N=1 for each variable. Dog bone shaped samples, following ASTM D638-14 design shape for tensile testing of plastics, were printed with two shells, and four top and bottom solid layers with the percent infill adjusted from 10% to 100% in 30% increments. The layer heights for the dog bone samples were printed at 0.15 mm. This makes the solid top and bottom four layers only 37.5% of the total sample thickness, with the infill making up 62.5% of the sample. Shear samples were printed with 10 shells and four top and bottom solid layers, with the layer height adjusted from 0.10 mm to 0.30 mm in 0.05 mm increments. Both tensile and shear samples had the infill printed at 45° angles that inverted or rotated between each layer, so if the first layer was at 45°, then the second layer was at −45°, and so on. FIGS. 3A and 3B plot results for a dog bone shaped test sample 40 (with a necked central portion 44 arranged between two wider end portions 42) as shown in FIG. 3C. FIG. 3B further includes a curvefit equation and coefficient of determination ($R^2$) value. FIGS. 3D and 3E plot results for a shear testing sample 50 shown in FIGS. 3F and 3G. All data have an error of 0.5% or less; error was determined by testing the INSTRON® tool with calibrated weights before testing. Samples were tested on the INSTRON® model 4411 to provide greater accuracy at the lower force levels.

The shear testing sample 50 was prepared and tested to determine the strength of different printing layer heights. FIGS. 3F and 3G show the shape of the shear testing sample 50 and the direction of printing, indicated by the bold arrow in FIG. 3F. The shear testing sample 50 was created with two s-shaped bars 51A, 51B each including a horizontal outer section 52A, 52B, an angled (non-horizontal) middle section 54A, 54B, and a horizontal inner section 56A, 56B that allow a square 58 in the center of the bars 51A, 51B to align with the horizontal direction of applied tensile force. This printing direction causes the layers within the square 58 to be subjected solely to the applied tensile force. This allows the strength of each layer thickness to be determined. The shear testing sample 50 was made with ten shells instead of two to ensure that there would be no deformation in the bars 51A, 51B like there was in the dog bone shaped test sample 40. The increase in shells allowed for more layers in the direction of the applied force to create a stronger tensile modulus.

The results from the dog bone shaped test and shear testing samples 40, 50 show that print settings can affect the strength of the design and portray unique performance characteristics for the layer height when using Taulman 680 FDA filament. The dog bone shaped test sample performance curves follow a trend of increased strength with increased percent infill. Using 100% infill was chosen since it provided the greatest strength and created the densest part. Having a denser part allowed the device to absorb more energy and be more durable for the user. The dog bone shaped test samples were designed to match the ASTM D638-14 for testing tensile strength of plastics; this way, the tensile strength of FFF 3D printed parts could be compared to plastic injected or molded parts.

Individual tensile dog bone shaped test samples demonstrate an unusual characteristic just after peak load is collected. The dog bone shaped test samples did not follow a continuous decline in load; instead, each sample began to fail, then stabilized, and then continued its failure. This stabilization is believed to be due to the fact that the infill layers collapse, thereby become more aligned with the loading direction, and then fail as a whole unit. This effect is not seen as substantially at the lower percent infill (i.e., 10%), since the reduced infill layer percentage was small and had little influence over the strength of the sample.

Results from the shear testing showed a unique curve that was not originally anticipated. FIG. 3D shows a parabola curve for peak layer height (LH) strengths, whereas a linear curve was original anticipated. The results show that the thickest layer height, 0.30 mm, had the strongest shear strength, 0.20 mm layer height had the weakest shear strength, and there is a gradual increase in shear strength as the layer height heads toward 0.10 mm. All samples failed within the square, demonstrating that the square received the applied force. This parabola curve appears to confirm that a thicker layer height was strongest since it had a greater cross-sectional area compared to the smaller layer heights. With the smaller layer height, there was greater layer fusion and a decrease in moment generated, which caused an increase in strength. While the middle sample, 0.20 mm, is the weakest since it had a smaller cross-sectional area (CSA) compared to the 0.30 mm layer, it had less layer fusion and a greater moment generated during testing compared to the lower layer height. The interplay of both smaller CSA and greater moment caused the 0.20 mm layer to have the weakest shear strength. These results show a consistency with engineering mechanics and material science.

No samples were printed at a layer height below 0.10 mm because the machine had not been tested to accurately and consistently print below this height. The MAKERGEAR® M2 printer was capable of printing at layer heights less than 0.10 mm, but such printing would require modifications to the machine and many printing trials to produce parts at that thickness level. Accordingly, no samples below 0.10 mm were printed to eliminate the variable of inconsistency.

Following these results, the optimum percent infill of 100% and layer height of 0.15 mm were chosen for printing of osseointegratable prosthetic device samples. A 100% infill value was chosen to provide the highest strength and the layer height of 0.15 mm was chosen for providing a tradeoff of print time and detail accuracy. Printer settings on the MAKERGEAR® printing apparatus were a printing speed of 600 mm/min, an extruder temperature of 267° C., a print bed at 100° C., and auto generated supports. The chosen speed and temperatures provided the best print quality with a maximum printing time of 17 hours.

Scaffold portion designs were evaluated with SOLID-WORKS® finite element modeling (FEM) software. Four different generally cylindrical scaffold designs shown in FIGS. 4A-4E were evaluated: a simple four-fin design (FIG. 4A), a four fin with center rod design (FIG. 4B), a four fin with a center rod and multiple transverse ribs design (FIG. 4C), and a four fin with center rod and helical ribs (FIGS. 4D and 4E). As shown in FIG. 4A, a scaffold portion 60 includes first and second cylindrical end portions 61, 62 joined by four longitudinal fins 64 that meet along a longitudinal axis 63 (e.g., a core of zero or near-zero diameter), with the longitudinal fins 64 being separated by longitudinally oriented recesses 65 each having a generally sector-shaped cross-section. FIG. 4B depicts another scaffold portion 70 that includes first and second cylindrical end portions 71, 72 that are joined by four longitudinal fins 74 that meet along a longitudinal core or center rod 73 having a non-zero diameter, with the longitudinal fins 74 being separated by longitudinally oriented recesses 75 each having a modified sector-shaped cross-section. FIG. 4C depicts yet another scaffold portion 80 that includes first and second cylindrical end portions 81, 82 that are joined by four longitudinal fins 84 that meet along a longitudinal core or center rod 83 having a non-zero diameter. The longitudinal fins 84 are separated by longitudinally oriented recesses 85 in a manner similar to the scaffold portion 70 of FIG. 4B, but with the addition of multiple transverse ribs 86 within the longitudinally oriented recesses 85 spanning between the longitudinal fins 84. FIGS. 4D and 4E illustrate another scaffold portion 90 that includes first and second cylindrical end portions 91, 92 that are joined by four longitudinal fins 94 that meet along a longitudinal core or center rod 93 having a non-zero diameter. The longitudinal fins 94 are separated by longitudinally oriented recesses 95 in a manner similar to the scaffold portion 70 of FIG. 4B, but with the addition of a helix-shaped rib structure or helical ribs 96 within the longitudinally oriented recesses 95 and spanning between the longitudinal fins 94.

Results of the FEM modeling of the foregoing four scaffold portion designs are shown in FIG. 4F. This FEM evaluation was conducted to determine which scaffold designs having a finned screw shape would work best in a 3D printed osseointegratable screw. The ideal design was determined to be finned screw with center rod and ribs ("transverse ribbed design"). The helical rib design did provide an overall stronger design, but the helical rib covered too much of the surface to allow area for tissue scaffolding. In contrast, the transverse ribbed design provided a strength increase, but did not obstruct the area for tissue scaffolding, and provided multiple anchor points for such scaffolding.

After characterizing the material and determining which of the four proposed scaffold portion designs was most beneficial, osseointegratable prosthetic device samples were printed with an overall diameter of 20.00 mm with a 2.50 mm thread pitch. The devices were produced to match the current overall diameter titanium sleeves that are commonly used. Tensile and three-point bending tests with a sample size of N=1 were performed on the osseointegratable prosthetic device samples with the INSTRON® model 1331 since the device had absorbed 6568.33 N (1476.62 lbs) in tension and 5256.37 N (1181.68 lbs) in bending before failure, which exceeded the load cell of the 4411 model. A small sample size was used due to the long print times, and material and testing equipment availability.

Osseointegratable prosthetic device samples according to a three-fin design (as shown in FIG. 5A) and a four-fin design (as shown in FIGS. 6A and 6B), each having ribs and a center rod of nine millimeters in diameter, were fabricated for testing. Details and fabrication of the respective devices are described below in connection with FIGS. 5A-6C.

Referring to FIG. 5A, a first osseointegratable prosthetic device 100 includes a body structure 100A having an insertion end 101 and an opposing external interface end 102. The body structure 100A includes an externally threaded anchor portion 103 proximate to the insertion end 101, a tool interface portion 111 proximate to the external interface end 102, and a scaffold portion 106 arranged between the externally threaded anchor portion 103 and the tool interface portion 111. The externally threaded anchor portion 103 includes a threaded outer surface 105 and a tapered conical section 104 proximate to the insertion end 101. The scaffold portion 106 includes a cylinder-shaped longitudinal core (or center rod) 108 that extends between the externally threaded anchor portion 103 and the tool interface portion 111 and that includes three longitudinally oriented fins 109 that extend radially outward from the core or rod 108. The fins 109 may include an outer diameter and external threads that substantially match an outer diameter and thread pitch, respectively, of the externally threaded anchor portion 103. The fins 109 are separated by recesses 107 that also contain multiple (e.g., five) transverse ribs 110 that extend between the fins 109. Each transverse rib 110 may have a radial dimension that is smaller than a radius of the fins 109. The recesses 107 of the scaffold portion 106 are configured to permit ingrowth of skeletal tissue. In certain embodiments, a plurality of apertures may be defined in the longitudinal fins 109 (e.g., in a circumferential direction) to aid in attachment of skeletal bone tissue. In certain embodiments, at least some recesses 107 may contain porous material (which may be fabricated contemporaneously with the body structure 100A or added later), organic material, and/or cellular material, with one or more of the foregoing materials preferably being arranged to promote skeletal bone ingrowth and/or attachment to the scaffold portion 106. In certain embodiments, the scaffold portion 106 includes a maximum width or outer diameter that is no greater than a maximum width or outer diameter of the externally threaded anchor portion 103.

The tool interface portion 111 (which may embody a hexagonal bolt-type head or other suitable shape) includes at least one tool-receiving surface 112 proximate to the external interface end 102. In certain embodiments, the tool interface portion 111 includes an exterior shape configured to receive a complementarily shaped inner surface of a rotary tool such as a wrench or a socket arranged to be rotated with a ratchet handle or drill. In other embodiments, the tool interface portion 111 may include an interior shape configured to receive a complementarily shaped outer surface of a tool such as an Allen wrench or the like. As illustrated in FIG. 5A, in certain embodiments, a flange surface 114 is arranged between the tool interface portion 111 and the scaffold portion 106, wherein the flange surface 114 comprises a maximum transverse dimension that exceeds a maximum transverse dimension of the scaffold portion 106. In certain embodiments, the flange surface 114 is defined in part by first and second radially extending flange elements 113A, 113B that are discontinuous relative to one another. The flange surface 114 may be used to contact a bone end surface upon sufficient rotation threading of the osseointegratable prosthetic device 100 into a cavity drilled into a bone, and thereby effectuate pretensioning of the device 100 (e.g., to promote retention of the device 100 and apply tension to the surrounding bone). A horizontal base member or platform 118 as shown in FIG. 5A may be formed concurrently with the first osseointegratable prosthetic device 100 as an artifact of the 3D printing process, but may be removed thereafter to prepare the device 100 for use.

As shown in FIGS. 6A and 6B, a second osseointegratable prosthetic device 120 includes a body structure 120A having an insertion end 121 and an opposing external interface end 122. The body structure 120A includes an externally threaded anchor portion 123 proximate to the insertion end 121, a tool interface portion 131 proximate to the external interface end 122, and a scaffold portion 126 arranged between the externally threaded anchor portion 123 and the tool interface portion 131. The externally threaded anchor portion 123 includes a threaded outer surface 125 and a tapered conical section 124 proximate to the insertion end 121. The scaffold portion 126 includes a cylinder-shaped longitudinal core (or center rod) 128 that extends between the externally threaded anchor portion 123 and the tool interface portion 131 and that includes four longitudinally oriented fins 129 that extend radially outward from the core or rod 128. The fins 129 may include an outer diameter and external threads that substantially match an outer diameter and thread pitch, respectively, of the externally threaded anchor portion 123. The fins 129 are separated by recesses 127 that also contain multiple (e.g., five) transverse ribs 130 that extend between the fins 129. Each transverse rib 130 may have a radial dimension that is smaller than a radius of the fins 129. Each transverse rib 130 also includes radial wall surfaces 136. In certain embodiments, one or more apertures 137 (shown in FIG. 6A) may be defined in a longitudinal direction through some or each of the transverse ribs 130. The recesses 127 and apertures 137 of the scaffold portion 126 are configured to permit ingrowth of skeletal tissue. In certain embodiments, a plurality of additional apertures may be defined in the longitudinally oriented fins 129 (e.g., in a circumferential direction) to aid in attachment of skeletal bone tissue. In certain embodiments, at least some recesses 127 may contain porous material (which may be fabricated contemporaneously with the body structure 120A or added later), organic material, and/or cellular material, with one or more of the foregoing materials preferably being arranged to promote skeletal bone ingrowth and/or attachment to the scaffold portion 126. In certain embodiments, the scaffold portion 126 includes a maximum width or outer diameter that is no greater than a maximum width or outer diameter of the externally threaded anchor portion 123.

The tool interface portion 131 (which may embody a hexagonal bolt-type head or other suitable shape) includes at least one tool-receiving surface 132 proximate to the external interface end 122. In certain embodiments, the tool interface portion 131 includes an exterior shape configured to receive a complementarily shaped inner surface of a rotary tool such as a wrench or a socket arranged to be rotated with a ratchet handle or drill. In other embodiments, the tool interface portion 131 may include an interior shape configured to receive a complementarily shaped outer surface of a tool such as an Allen wrench or the like. As illustrated in FIGS. 6A and 6B, in certain embodiments, a flange surface 134 is arranged between the tool interface portion 131 and the scaffold portion 126, wherein the flange surface 134 comprises a maximum transverse dimension that exceeds a maximum transverse dimension of the scaffold portion 126. In certain embodiments, the flange surface 134 is defined in part by first and second radially extending flange elements 133A, 133B that are discontinuous relative to one another. The flange surface 134 may be used to contact a bone end surface upon sufficient rotation threading of the second osseointegratable prosthetic device 120 into a cavity drilled into a bone, and thereby effectuate preloading of the device 120 (e.g., to promote retention of the device 120 and apply tension to the surrounding bone). A horizontal base member or platform 138 as shown in FIGS. 6A and 6B may be formed concurrently with the second osseointegratable prosthetic device 120 as an artifact of the 3D printing process, but may be removed thereafter to prepare the device 120 for use.

For devices 100 and 120 as previously described, samples were 3D printed longitudinally (i.e., parallel to the direction of applied tension) to provide the greatest strength, since printing perpendicular to the direction of applied tension would result in a weaker part due to the layer adhesion strength of FFF parts. FIG. 5B is a table providing area, volume, and dimension data for the first (fused filament fabrication 3D printed) osseointegratable prosthetic device 100 of FIG. 5A. Similarly, FIG. 6C is a table providing area, volume, and dimension data for the second (fused filament fabrication 3D printed) osseointegratable prosthetic device 120 of FIGS. 6A and 6B.

Three-fin and four-fin osseointegratable prosthetic device samples according to the designs of FIGS. 5A, 6A, and 6B were tested to assess their maximum tension and three-point bending strength. The osseointegratable prosthetic device samples were threaded into four M20×2.50 steel nuts each having a nickel coating to simulate a rigid fixation that will be seen when such devices are fully implanted into the bone canal of a patient. For the three-point bending tests, the osseointegratable prosthetic device samples were separately tested with the applied force perpendicular and parallel to the flange, respectively, since the flange is a partial flange and does not completely wrap around the head of the tool interface portion. As stated previously, each flange includes first and second radially extending flange elements that are discontinuous relative to one another. The discontinuous nature of the flange elements alters bending resistance of the osseointegratable prosthetic device, depending on the direction of applied force.

FIGS. 7A and 7B provide plots of tensile and three-point bending sample force versus displacement results, respectively. A force versus displacement graph was used to allow for easier comparison to results from literature on osseointegrated prosthetics. Specifically, FIG. 7A provides plots of tension force (N) versus displacement (mm) for the fused filament fabrication 3D printed osseointegratable prosthetic devices of FIG. 5A (dotted line) and of FIGS. 6A and 6B (dash line), and FIG. 7B provides plots of tension force (N) versus displacement (mm) for the fused filament fabrication 3D printed osseointegratable prosthetic devices of FIG. 5A (dash line is three-fin parallel, and dotted line is three-fin perpendicular) and of FIGS. 6A and 6B (dash-dot line is four-fin parallel, and solid line is four-fin perpendicular). In both tension and bending, the second (four-fin) osseointegratable prosthetic device 120 according to FIGS. 6A and 6B performed better in tension than the first (three-fin) osseointegratable prosthetic device 100 according to FIG. 5A, due to the increase in cross-sectional area (CSA). In each instance, application of force parallel to the flange resulted in a higher resistance to bending due to the increase in area moment of inertia.

Three-point bending samples were tested in a nonconventional way, using the test fixture 140 shown in FIGS. 8A and 8B, to demonstrate the strength of osseointegratable prosthetic devices samples in a more realistic implant environment instead of the standard three-point bending test. An INSTRON® Model 1331 (maximum load cell capability of 10,000 lbs) testing rig 141 was used, with vertical piston arms 142 supporting a horizontal cross-bolt 146 serving as the load applying surface. A screw-shaped device sample 148 was threaded into four steel nuts 149 and then rested on a U-shaped support base 143 (including a square tubular horizontal base member 145 and vertical riser members 144 serving as laterally spaced load supports). Contact points were 22.60 mm and 38.00 mm from the applied force, with the smaller distance being the contact point for the head of the screw-shaped device sample 148. The nut 149 closest to the flange of the device sample 148 had a sleeve fixed to its surface where the test fixture 140 could push while inserted into the sleeve. This allowed the applied force to always be applied downward on the device sample 148 and not slip off in one direction.

For the three-point bending test, the device samples 148 were tested with the applied force perpendicular and parallel/inline to the flange. The flange was not created to wrap around the entire screw-shaped body structure to ensure a minimal design that could leave additional area for possible skin/skeletal muscle scaffolding onto the head of the screw for future prototypes to reduce infections. The bending samples with the applied force parallel to the flange had the greatest strength due to the larger cross-sectional area and area moment of inertia.

Tensile tests were also performed. After a device sample was threaded into the four steel nuts, the head (tool interface portion) of the device sample was clamped into an INSTRON® tensile testing rig, and then an upper part of the interface portion surface was grabbed to enable tensile testing. Samples failed just beneath the head (tool interface portion) of the device sample, within the fins and center rod of the scaffold portion, and with linear fracture lines created perpendicular to the applied force. All samples failed appropriately within the smaller cross-sectional area and demonstrated a brittle type of fracture with little yielding. This property is not consistent with polyamide six-based materials in general, but since the Taulman 680 FDA is a cross-linked polyamide six material, an appropriate trend was observed. All samples failed with tension on the distant edge and compressed on the near edge of the applied force.

FIG. 17A is a table providing maximum displacement and force values for M14 and M20 3D printed osseointegratable screws threaded into cadaver humeral samples. FIG. 17B is a table identifying differences between M14 and M20 3D printed osseointegratable screws threaded into cadaver humeral samples to M14 and M20 3D printed osseointegratable screws threaded into simulated steel nuts.

The osseointegratable prosthetic devices 100, 120 according to FIGS. 5A, 6A, and 6B were designed to meet the average force seen at the wrist of 500.00 lbs or 2.20 kN at an average fall height and up to a maximum value of just over 900.00 lbs or 4.00 kN at a fall height of six meters. The force seen at the wrist was chosen since it sees the greatest force during a fall. The shoulder and elbow experience less force because they have the degree(s) of freedom to displace during a fall and decrease the force seen at that joint and subsequent body parts around them. However, the wrist makes a hard contact with the ground during a fall and provides no deflection on contact with a surface.

Additionally, torque-to-failure with initial creep tests were performed to demonstrate the storage of linear tension generated by torsion and the maximum seating torque. FIG. 7C is a plot of the seating and break-off torques and torque-to-failure values. The FFF osseointegrated screws were seated to 3.00 Nm, given five minutes to settle, loosened to remove tension, and then the foregoing steps were repeated two more times. After performing the creep tests, the samples were taken to failure. The seating torque value needed to fall between 4.00 Nm and 0.50 Nm, representing a secure and loose fitting implant for insertion. These seating values represent osseointegrated titanium prosthesis used for femur attachment. Femur attachments require higher strength and seating values than humerus attachment, therefore, using these as a requirement confers a safety factor to the osseointegratable device designs disclosed in FIGS. 5A, 6A, and 6B. Additional creep and torsion testing were performed to demonstrate that osseointegratable prosthetic devices according to the foregoing designs could be repeatedly seated at a torque and backed off after a settling time, yet still be within the range of a loose-fitting to a tight-fitting osseointegrated prosthetic. The anchor portion needs to be able to be seated during the rehabilitation process to allow for bone growth into the scaffold area. If the anchor portion rotates during this process, then the bone that has currently formed will be broken and displaced, causing the bone fixation to be remodeled. Once the bone has formed far enough into the voided areas (i.e., recesses between fins), it will prevent the anchor portion from being rotated accidently during the rehabilitation process. All seated samples had a maximum decrease of 26.70% from the original seated torque to the back-out torque. Additionally, all samples had a maximum failure of 6.80 Nm-7.3 0 Nm, which embody values above the ideal tight fitting implant of 4.00 Nm.

The osseointegratable prosthetic device characterized herein has a bending stiffness (K) of 769.26 N/mm within the simulated environment at a maximum displacement of 6.833 mm, and a bending moment (M) of 118,793.74 Nmm (118.79 Nm) to screw head (Mh) and 199,741.69 Nmm (199.74 Nm) to steel nut contact (Mn). Extrapolating this data out to the forces seen in the Welke et al. (i.e., Welke B, et al. Stiffness and ultimate load of osseointegrated prosthesis fixations in the upper and lower extremity. Biomed Eng Online 2013; 12:70) a 3D printed osseointegratable device according to certain embodiments would be able to hold 12.14% more load at the same moment distance as the synthetic humeri and 69.11% more load at the same moment distance as the cadaver humeri. The cadaver and synthetic humerus bones have bending moments of 36.7 Nm and 104.9 Nm, respectively.

In certain embodiments, a 3D printed osseointegratable device has a pull-out strength of 6,568 N, which is larger than the reported axial pullout strength of cemented osseointegrated prosthesis in a femur and is larger than the reported pull out forces seen on a sheep animal model of an osseointegrated prosthetic at 1) time zero before bone ingrowth and 2) three months after bone ingrowth. This disclosure is only comparing the values of titanium cemented and seat osseointegrated prosthetics to demonstrate that the 3D printed osseointegratable prosthetic device has similar or improved fixation tensile strength in its working environment. The osseointegrated prosthesis, titanium, or the 3D printed device presented here would fail at the bone-prosthetic interface prior to maximum loading of the cortical bone, where the tensile strength of an average humeri bone is approximately 40,000 N, using an average adult cross-sectional area and stress of 125 MPa for humeri bone.

This osseointegratable prosthetic device can withstand loads greater in bending than what the skeletal bone can handle, causing the bone to break before the FFF 3D printed screw does, even with the large cavities designed for large volume of bone ingrowth. This increases the likelihood that the screw will not fail and cause an open wound to the user that could lead to severe heath concerns.

Additionally, the screw has an elastic modulus of only 0.197 GPa, meaning that stress shielding will be seen significantly less than in its titanium counterparts. This will result in bone continuing to form instead of reabsorbing and removing itself from the site of the implant. Having this effect is beneficial for bone tissue growth since the area will continually see stress and will keep building/rebuilding bone cells at the site, preventing prosthetic loosening. Having an elastic modulus well below that of bone has been shown to prevent stress shielding when using polyether ether ketone material (PEEK); which has an elastic modulus of only 3.6-3.9 GPa.

Since osseointegratable prosthetic devices according to certain embodiments are designed to be 3D printed, the shape can be modified to create a part that is patient-specific for point-of-care. This allows for different osseointegratable prosthetic device sizes to accommodate all variations in skeletal systems. Additionally, child-sized osseointegratable prosthetic devices are contemplated to be implantable at a much younger age and stay within patients for their entire lives.

Throughout the FFF printing process, minor issues were encountered when printing. First, printing was performed at a much higher temperature than what is recommended from the Taulman 3D site of only 238° C. Print temperatures of 267° C. were used to get high-quality prints with the semi-transparent very light tan finished parts. Secondly, printing was performed with a solid 0.90 mm thick platform on the bottom of the CAD model file to ensure that threaded surfaces would stick since they were the first layer on the platform. Additionally, the parts were modeled and printed with an overall diameter of 19.00 mm and a thread pitch of 2.55 mm due to tolerances in the machine and material expansion during printing.

In certain embodiments, a method of fabricating the osseointegratable prosthetic device as described herein is provided, wherein the method comprises: heating a thermoplastic material to a flowable state; and selectively depositing the heated thermoplastic material in sequential layers to form the body structure including the externally threaded anchor portion, the tool interface portion, and the scaffold portion; wherein the body structure embodies a unitary, fused polymeric body structure.

In certain embodiments, a method for facilitating attachment of a prosthetic limb to a mammalian user is provided, wherein the method comprises: defining a cavity in a bone of the mammalian user, and threading the osseointegratable prosthetic device as described herein into the cavity. Such threading may be performed by applying a tool to the tool interface portion, and applying torque to the osseointegratable prosthetic device.

Mechanical interaction between 3D printed osseointegratable prosthetic devices of different sizes and cadaver skeletal samples were also examined.

Fresh frozen non-preserved cadaver samples were donated by the MORE Foundation and were of a 68-year-old male at 73 inches in height and a body weight of 230 lbs, and a 67-year-old male at 71 inches in height and a body weight of 250 lbs. A total of three cadaver samples were donated for testing. Cadaver samples were stored at −20° C. but were tested at −10° C. due to transportation and temporary storage of the samples during testing. Samples were kept in an insulated cooler while three-point bending and torsion tests were performed.

Cadaver samples were dimensionally analyzed to determine the outer diameter of the FFF 3D printed osseointegration screw for testing. FIG. 9A is a first photograph of a humeral sample obtained from a cadaver to enable testing of 3D printed osseointegratable screw prototypes according to one embodiment of the present disclosure. FIG. 9B is a second photograph of the humeral sample of FIG. 9A, with addition of rectangles 151-153 identifying upper, middle, and lower regions, respectively, of the sample. The three regions 151-153 were identified for each of the three different cadaver samples. The three different cadaver samples had dimensions as listed in FIG. 16, which shows the minimum and maximum diameters measured in each region. Since the cadaver samples did not have perfectly round shapes, the minimum and maximum dimensions were needed to appropriately determine the size of 3D printed osseointegratable devices that could be implanted. Sample 1 and Sample 2 had similar shapes and dimensions, while Sample 3 had much larger portions seen at the middle and upper regions 152, 151 of the cadaver humerus. Sample 3 had an average increase of 66%, 45%, and 15% in the upper, middle, and lower regions 151-153 compared to Samples 1 and 2. Cadaver samples were taken from the middle region 152 of each humerus, and then cut and threaded.

After reviewing the cadaver sample dimensions, it was determined that Samples 1 and 2 would receive an M14×2.0 osseointegratable screw and Sample 3 would receive an M20×2.5 mm osseointegratable screw. The M14×2.0 mm and M20×2.5 mm sizes were used because they embody standard thread sizes and profiles used in practice and industry, while the M20×2.5 mm matches the outer diameter used in current titanium osseointegration screws. The M14 screw size was only scaled down in the x-axis and y-axis, leaving the z-axis (or overall length) unchanged.

For three-point bending tests, Samples 1 and 2 were tested with 14 mm outer diameter osseointegratable screws instead of the 20 mm diameter osseointegratable screws due to the cadaver sample dimensions. Given the three available cadaver samples including two with smaller samples of similar dimensions, the smaller samples were chosen for the three-point bending tests. Additionally, using the 20 mm diameter screw on the smaller samples would not have been possible, since the cadaver samples would be destroyed in the process. Therefore, the three-point bending tests used simulated and cadaver samples to show the changes from a simulated (steel) to an implant-like environment. Restated, the single M20 osseointegratable screw was used as the comparison to our simulated steel environment torsion data collected and the two M14 osseointegratable screws were used as the comparison to the simulated steel environment three-point bending data collected previously.

Tested samples comprised a four-fin design with a center rod and external ribs according to the design of FIGS. 6A and 6B. A partial flange design was used to develop a minimal design that could leave additional area for potential skin/skeletal muscle scaffolding onto the head of the screw for future prototypes to reduce infections. Samples were printed longitudinally or perpendicular to the direction of applied force during the three-point bending test to provide the greatest strength, since printing parallel to the direction of applied force would result in a weaker part due to the layer adhesion strength of FFF parts.

The M14×2.0 mm samples were threaded into five nickel coated steel nuts for simulated testing or threaded into cadaver samples, which were tapped and threaded to receive the M14×2.0 mm osseointegration screw. The samples were then tested for three-point bending strength with the applied force perpendicular and parallel to the flange design, since the flange was a partial flange and did not completely wrap around the head of the screw (see FIGS. 6A and 6B for the screw design and FIGS. 8A and 8B for the test fixture). The applied force parallel to the flange had a higher resistance to bending due to the increase in area moment of inertia and cross sectional area. The screws had contact points with the U-shaped test fixture of 22.60 mm and 38.00 mm from the applied force, with the smaller distance being the contact point for the head of the screw. The three-point bending test fixture described previously herein was used to provide a more realistic implant environment then compared to the standard three-point bending test.

FIGS. 10A and 10B provide the comparison results of three-point bending tests. FIG. 10A is a plot of displacement (mm) versus applied compressive force (N) for three-point bending of M14 and M20 3D printed osseointegratable screws according to the present disclosure threaded into cadaver humeral samples, as well as simulated data for M14 3D printed osseointegratable screws threaded into steel nuts, with the applied force perpendicular and parallel to the partial flange design. FIG. 10B represents a subset of data plotted in FIG. 10A, embodying a plot of displacement (mm) versus applied compressive force (N) for three-point bending of M14 3D printed osseointegratable screws threaded into cadaver humeral samples, as well as the simulated data for M14 3D printed osseointegratable screws threaded into steel nuts. FIG. 10C is a perspective view of a 3D printed osseointegratable screw according to one embodiment, with a solid arrow showing a direction of applied bending force extending parallel to first and second radially extending flange elements of the osseointegratable screw (thereby representing an increased cross-sectional area), and with a dashed arrow showing a direction of applied bending force extending perpendicular to the first and second radially extending flange elements (thereby representing a reduced cross-sectional area). In FIGS. 10A and 10B, force versus displacement graphs were used to allow for easier comparison to literature on osseointegrated prosthetics. The above-outlined M20×2.5 mm simulated steel environment bending test recorded a maximum of 5256.37 N (1181.68 lbs) in bending before failure, while the scaled-down M14×2.0 mm reported a maximum bending force of 2325.93 N (522.89 lbs) in the simulated environment. The M14×2.0 mm in the cadaver sample achieved a maximum bending force of 1609.76 N (361.89 lbs).

FIG. 11A is a side elevation view photograph of a portion of a M14 3D printed osseointegratable screw threaded into a cadaver humeral sample, following three-point bending failure, with the applied bending force extending parallel to first and second radially extending flange elements of the osseointegratable screw. FIG. 11B is a magnified front elevation view photograph of the osseointegratable screw and cadaver humeral sample of FIG. 11A, following three-point bending failure, with the photograph further including a ruler to provide an indication of length of the cadaver humeral sample and a head portion of the osseointegratable screw. FIG. 11C is a perspective view photograph of a central (e.g., scaffold) portion of the osseointegratable screw retained in the cadaver humeral sample of FIGS. 11A and 11B following three-point bending failure, with the applied bending force extending perpendicular to first and second radially extending flange elements of the osseointegratable screw. FIG. 11D is a side elevation view photograph of a tool interface portion of the osseointegratable screw of FIG. 11C following bending failure and removal from the central (scaffold) portion. FIG. 11E is a front elevation view photograph of the tool interface portion of FIG. 11D.

For the three-point bending results, the M14 screw had a maximum bending stiffness (K) of 292.69 N/mm and 262.04 N/mm within the simulated environment in the perpendicular and parallel orientations respectively. Within the cadaver environment, the screw had a maximum bending stiffness (K) of 147.82 N/mm and 146.49 N/mm in the perpendicular and parallel orientations respectively.

Additionally, the M14 FFF 3D printed screw had bending moments (M) of 25763.39 Nmm (25.76 Nm) and 52566.23 Nmm (52.57 Nm) to the screw head (Mh) in the perpendicular and parallel orientations respectively. The screw also had bending moments to 43318.97 Nmm (43.32 Nm) and 88385.69 Nmm (88.39 Nm) to the steel nut contact (Mn) within the simulated environment. In the cadaver environment, the screw had bending moments (M) of 22942.04 Nmm (22.94 Nm) and 36380.58 Nmm (36.38 Nm) to the screw head (Mh) in the perpendicular and parallel orientations respectively. The screw also had bending moments of 38575.11 Nmm (38.58 Nm) and 61170.89 Nmm (61.17 Nm) to the cadaver end contact point (Mn).

When extrapolating the maximum data values out to the forces and moment arms seen in Welke et al., the M14 printed screw would only be able to hold 50.11% and 34.68% of the load as the synthetic humeri compared to the simulated and cadaver environments respectively. Additionally, the screw would be able to hold 43.23% more of load compared to the cadaver values disclosed in Welke et al. in the simulated steel environment described herein and have nearly identical bending moment values with the cadaver environment results described herein being able to hold 99.13% of the applied load seen in Welke et al. The cadaver and synthetic humeri bones in Welke et al. have bending moments of 36.7 Nm and 104.9 Nm respectively.

The originally designed M20 FFF 3D printed screw had a bending stiffness (K) of 769.26 N/mm within the simulated environment at a maximum displacement of 6.83 mm, and a bending moment (M) of 118,793.74 Nmm (118.79 Nm) to screw head (Mh) and 199,741.69 Nmm (199.74 Nm) to steel nut contact (Mn). Extrapolating this data out to the forces seen in Welke et al., the printed screw would be able to hold 12.14% more load at the same moment distance as the synthetic humeri and 69.11% more load at the same moment distance as the cadaver humeri.

The original M20 screw was designed to meet the average force seen at the wrist of 500.00 lbs or 2.20 kN at an average fall height and up to a maximum value of just over 900.00 lbs or 4.00 kN seen at a fall height of six meters. As previously discussed, the force seen at the wrist was chosen since it sees the greatest force during a fall. The shoulder and elbow see less of a force because they have the degree(s) of freedom to displace during a fall and decrease the force seen at that joint and subsequent body parts around them. Where the wrist makes a hard contact with the ground during a fall and provides no deflection on contact with a surface. When looking at the maximum bending forces (indicated in FIGS. 10A, 10B, 17A, and 17B), we can see that the M20 screw can withstand the forces seen during a fall in either the simulated environment or even when applying the 12.29% decrease seen in the change from a steel nut to the cadaver sample from the M14 screw. In contrast, the M14 screw cannot withstand the average or maximum fall forces in either the simulated or cadaver environment, and could only withstand the average fall forces seen while in the parallel test orientation.

It would be recommended that the M14 FFF 3D printed screws be used for children or smaller individuals where their mass during a fall would have less impact. The children in this case could go through two surgeries in their lifetime to allow them to grow into the larger diameter screw if necessary. In contrast, the reference values from Chiu et al. (i.e., Chiu, James, and Stephen N. Robinovitch, "Prediction of upper extremity impact forces during falls on the outstretched hand," *Journal of biomechanics* 31.12 (1998): 1169-1176) use individuals with body masses of 51 kg (112.43 lbs) to 83 kg (182.98 lbs) and heights of 1.52 m (59.8 inches) to 1.78 m (70.07 inches).

The M14 screw samples that were tested in the parallel orientation had larger displacement values compared with the perpendicular orientation and the parallel orientation for the M20 sample due to the increase in flexibility caused by the change in length to diameter ratio. Since the overall screw lengths were kept the same and the outer diameter was changed from 20 mm to 14 mm, the flexibility increased as the diameter decreased.

Initial creep and torsion tests were also performed on the M20 screw in the cadaver sample. For the torsion testing, torque-to-failure with initial creep tests were performed to demonstrate the storage of linear tension generated by torsion and the maximum seating torque in the cadaver sample. Such testing was performed to demonstrate that the sample could be repeatedly seated at a torque, and then backed off after a settling time, and still be within the range of a loose and tight fitting osseointegrated prosthetic. As noted previously, the anchor portion of the osseointegratable device should be able to be seated during the rehabilitation process to allow for bone growth into the area dedicated for bone tissue scaffolding. Rotation of the device during this process could cause the newly formed bone to break off and displace, causing the bone fixation to be remodeled, whereas device rotation is prevented once the bone has formed enough into the scaffold portion (e.g., longitudinal recesses) of the device.

Seating and break-off torques and torque-to-failure values were established for the cadaver and simulated environment. The FFF osseointegrated screw was seated to 3.00 Nm, given five minutes to settle, then loosened to remove tension, and then the foregoing steps were repeated two more times. After performing the creep tests, the sample was taken to failure. Trials 1 and 3 of the cadaver testing were seated to 3.2 Nm instead of 3.0 Nm.

Figure 12A:
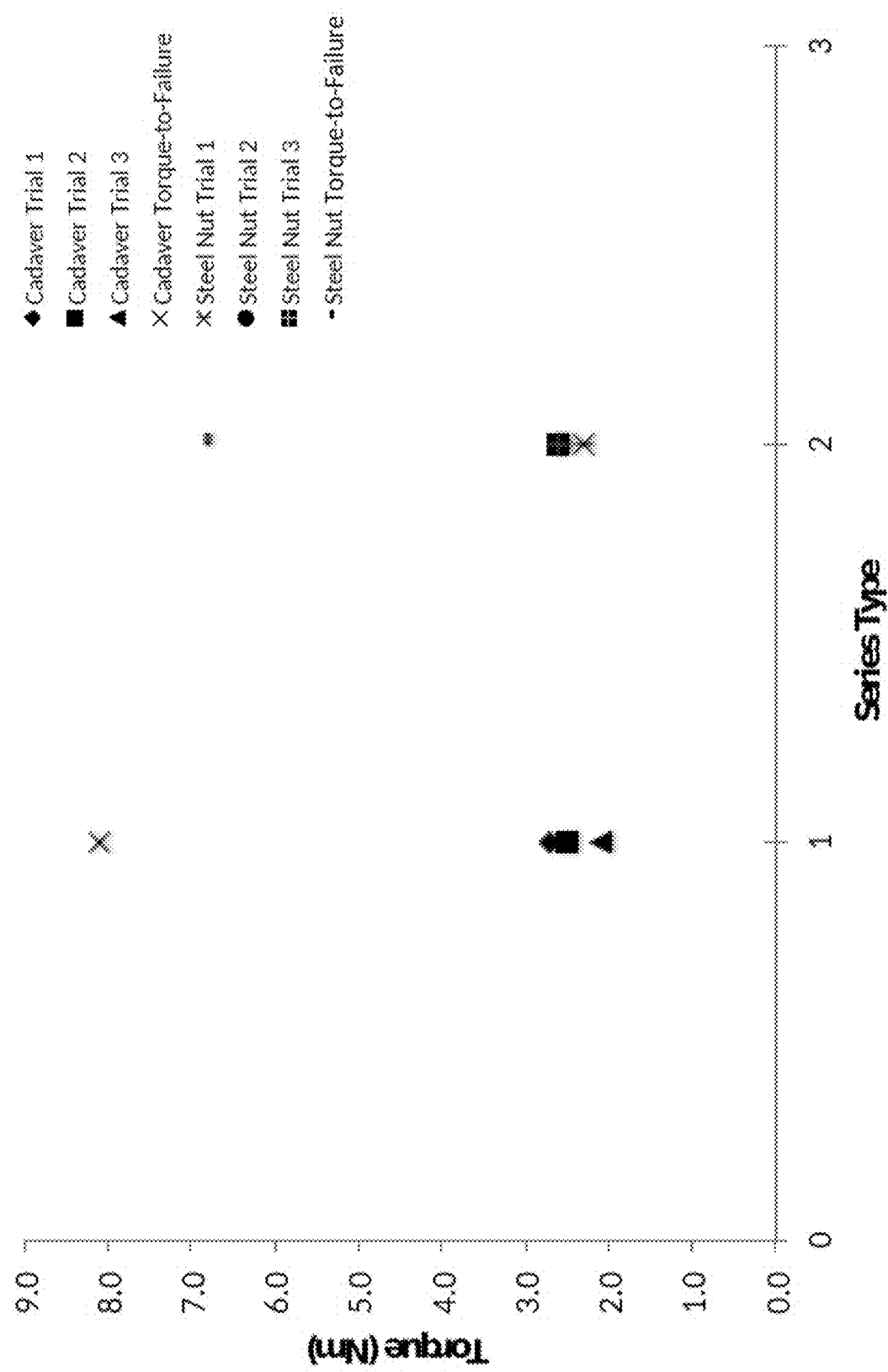
FIG. 12A is a plot of torque versus series type for torque to failure and creep testing of 3D printed osseointegratable screws threaded into cadaver humeral samples as well as simulated data for 3D printed osseointegratable screws threaded into steel nuts.
Figure 13A:
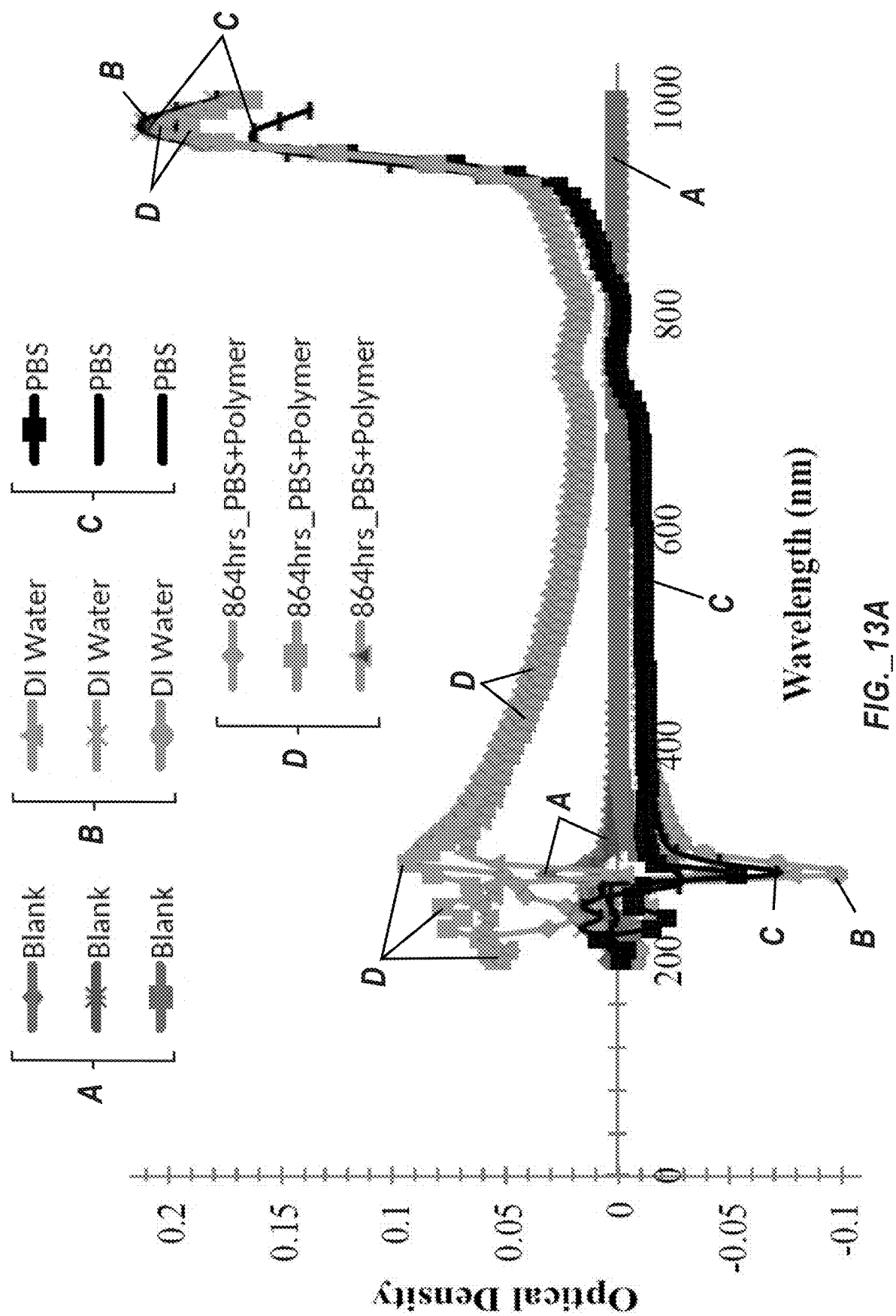
FIG. 13A is a plot of optical density versus wavelength (nm) for a polymer leaching study conducted with polyamide six 3D printed material in a phosphate buffer solution for incubation at 864 hours with a sample size of N=3.
Figure 13B:
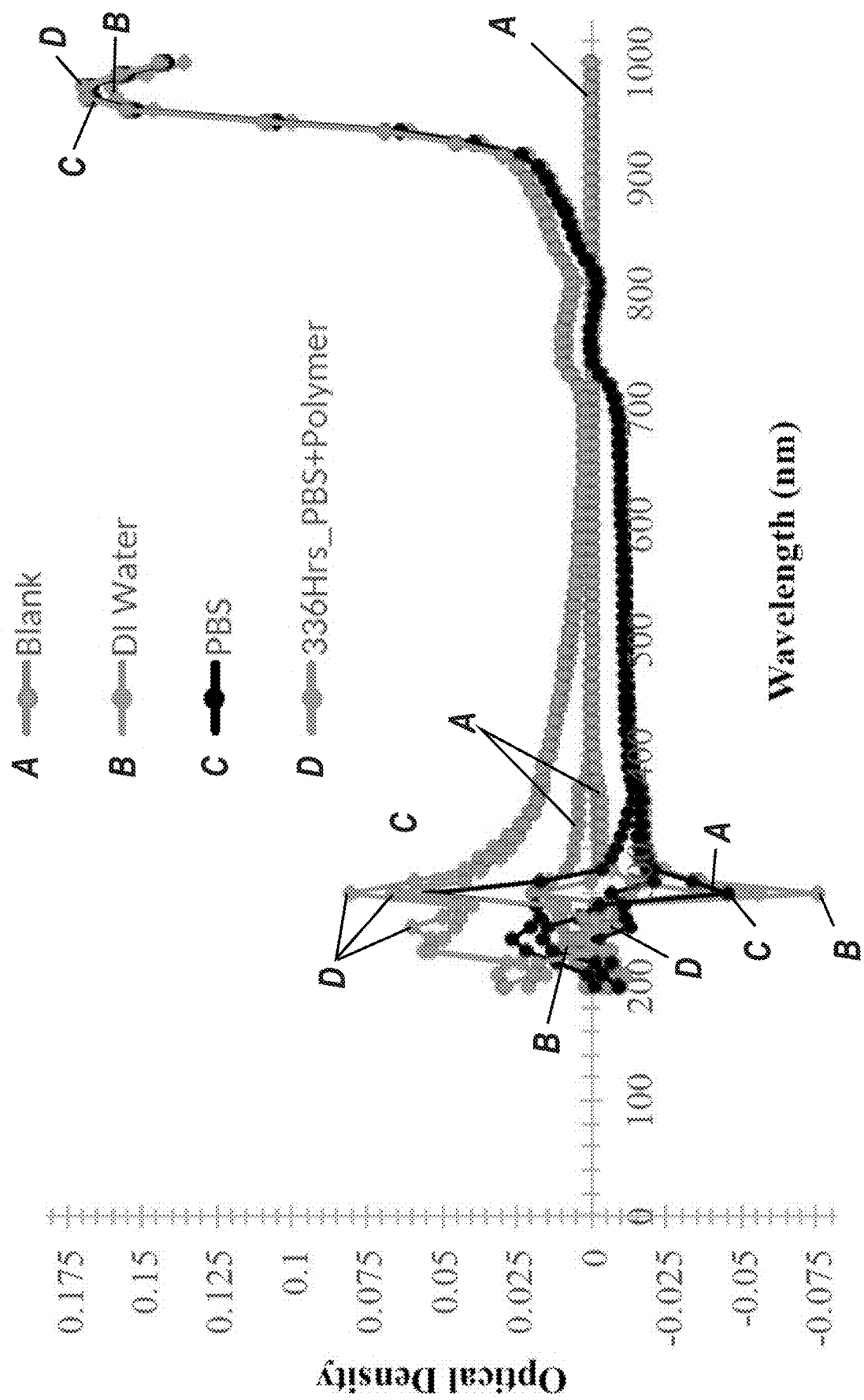
FIG. 13B is a plot of optical density versus wavelength (nm) for a polymer leaching study conducted with polyamide six 3D printed material in a phosphate buffer solution for incubation at 336 hours with a sample size of N=3.
Figure 13E:
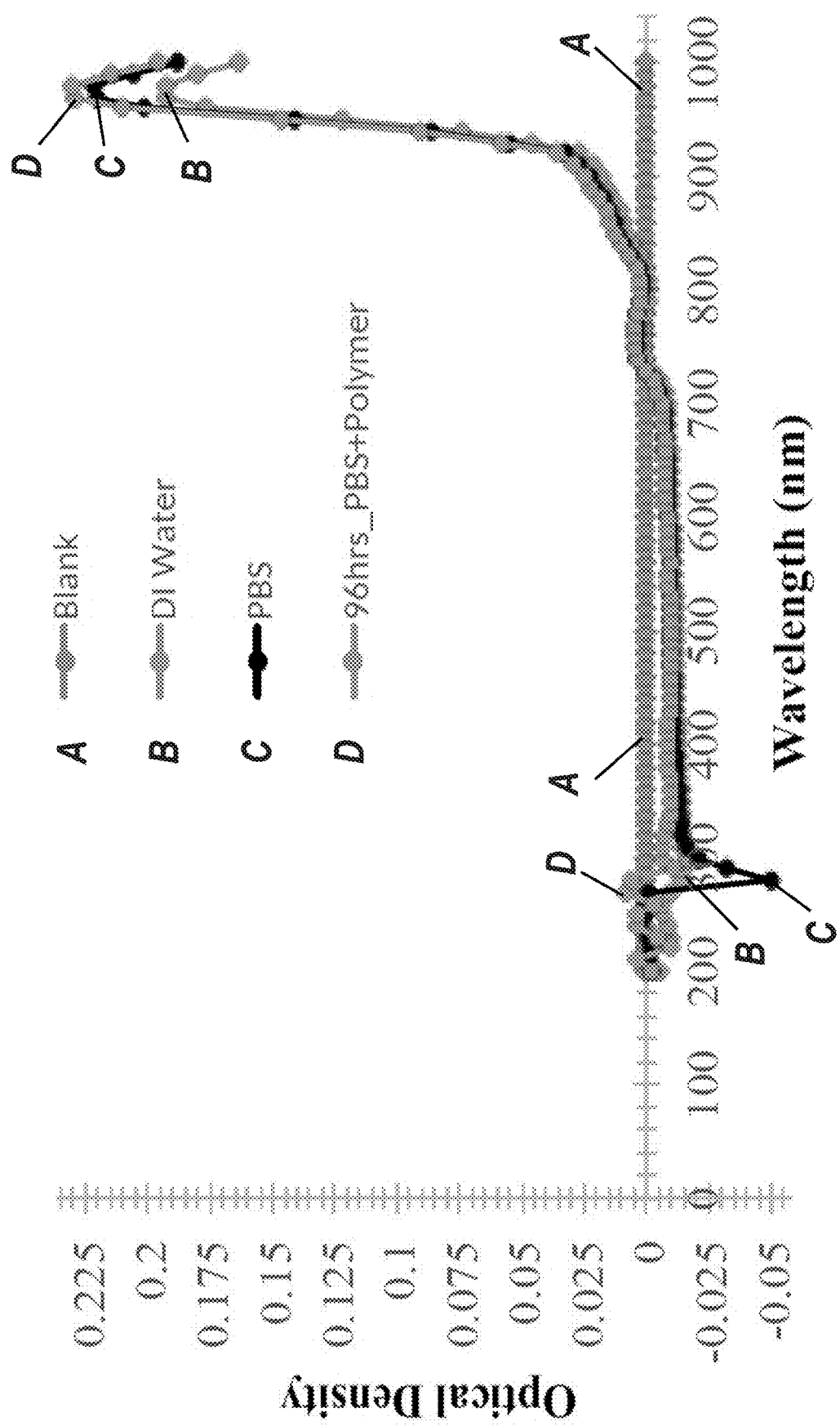
FIG. 13E is a plot of optical density versus wavelength (nm) for a polymer leaching study conducted with polyamide six 3D printed material in a phosphate buffer solution for incubation at 96 hours with a sample size of N=1.
Figure 13F:
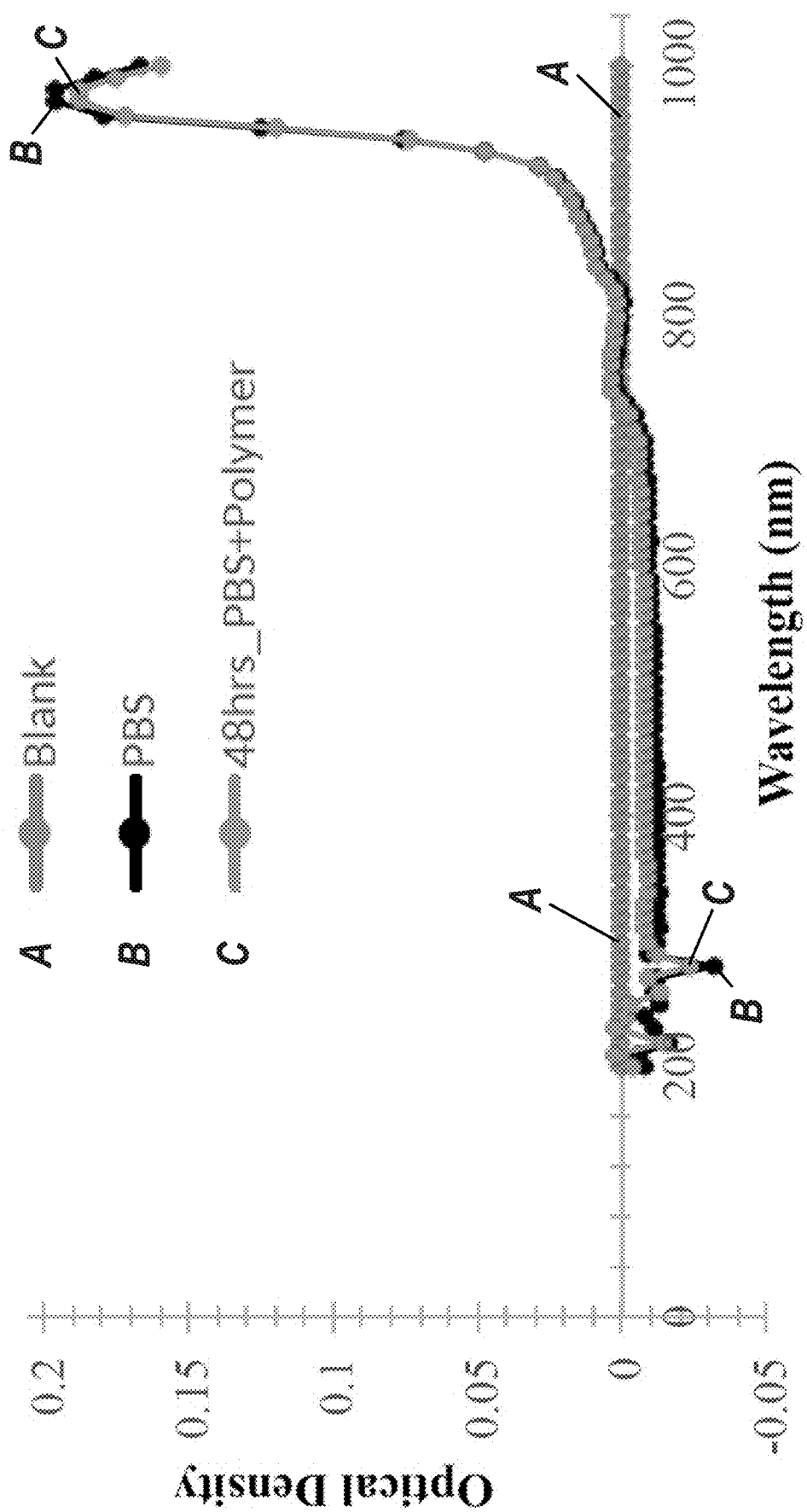
FIG. 13F is a plot of optical density versus wavelength (nm) for a polymer leaching study conducted with polyamide six 3D printed material in a phosphate buffer solution for incubation at 48 hours with a sample size of N=1.

FIG. 12A is a plot of torque (Nm) versus series type for torque to failure and creep testing of 3D printed osseointegratable screws threaded into cadaver humeral samples as well as simulated data for 3D printed osseointegratable screws threaded into steel nuts. The seated cadaver sample had a maximum decrease of 34.38% from original seated torque to the back-out torque, while the simulated sample had a maximum decrease of 26.70% from the original seated torque to the backout torque. Additionally, the cadaver and simulated sample had a maximum failure of 8.10 Nm and 6.80 Nm respectively, which is above the ideal tight fitting implant of 4.00 Nm. From the results, we can see the break-off torque values, trials 1-3, and torque-to-failure values for the cadaver and simulated steel nut samples. The data shows that the screw can be seated to well past what is considered a tight fitting prosthetic, a failure torque of 8.1 Nm and 6.8 Nm for the cadaver and steel samples respectively, and an average torque settling of 22.2% and 16.67% for the cadaver and simulate steel nut samples, respectively.

FIGS. 12B-12D are side view photographs of a 3D printed osseointegratable screw threaded into a cadaver humeral sample following torque insertion failure, resulting in fracture of the cadaver humeral sample.

The testing shows that there is minimal change in torsion values when going from a simulated to a cadaver environment. Additionally, the maximum bending force decreased 12.29% and the maximum displacement increased 43.28% when going from the simulated to the cadaver environment. The results also show that the smaller M14 screw is not suitable for adults with body masses between 51-83 kg and heights between 1.52-1.78 m, but may be suitable for children or small adults.

In addition to the foregoing developments, biocompatibility of 3D printed osseointegratable prosthetic devices was further examined, to determine the impact of the 3D-printed material on live cells, including steps of soaking polymeric material in cellular growth media. Potential toxicity of compounds that may be leached from the printed polymer material into the extracellular environment was investigated.

3D printed polymer was incubated in a phosphate buffer saline (PBS) solution and showed minimal change in optical density from baseline PBS testing after >30 days of incubation. Additionally, a cytotoxicity testing was performed and demonstrated that the polymer, once FFF 3D printed, had no measureable impact on the health and life of human osteo cells. Microscopy and flow cytometry methods were used to evaluate cell viability. These studies demonstrated initial positive results that a 3D printed osseointegratable device can be used as a long-term prosthetic attachment implant with minimal changes to mechanical properties when implanting in a cadaver sample.

Cytotoxicity of leached material into solution was determined using the U-2 OS human osteosarcoma cell line (ATCC HTB-96; "osteo cell line"). The osteo cell line was chosen since the osseointegratable prosthetic device comes into the greatest contact with skeletal bone cells, followed by skeletal muscle and skin cells. Since the device is expected to create a fixation point within the bone, the osteo cell testing was needed as the first step in determining that the device would not be rejected and would be able to generate the fixation point. Although U-2 OS has several genomic aberrations and is highly proliferative, the cells are still vulnerable to cytotoxins such as rotenone and tumorsuppressor activation. 3D printed rings and discs used for cytocompatibility testing were designed in SOLIDWORKS® 3D CAD software and printed using FFF 3D printing. Prior to performing cytotoxicity tests, the FFF 3D printed parts were sterilized using a STERIS® Autoclave SG-120 (Steris Inc., Temecula, Calif., USA). The samples were placed in Crosstek autoclave sealable bags and then were sterilized. Autoclave settings used were a one-minute purge followed by a 30 minute sterilization time at 121.0° C., then a 30-minute drying time under a 10.0 in Hg vacuum. Following sterilization, the bags were kept at room temperature until the cytotoxicity testing was performed.

U-2 OS cells were grown to 90% confluency in a T-75 flask in complete growth medium (McCoy's 5A, 10% fetal bovine serum, and 1% penicillin streptomycin) at 3TC in a 5% $CO_2$ humidified incubator. To generate treated medium, a 8 mL sample of sterilized FFF 3D printed material was incubated in 40 mL complete growth medium with slow agitation (30 rpm on a Labnet H5600 Revolver Rotator) at 4° C. for 72 hours to encourage leaching. This treated medium was applied to cultured U-2 OS cells and viability was measured after 48 hours. From an initial seeding density of ~25 cells/mm$^2$, the control and treated samples reached the expected coverage of ~100 cells/mm$^2$, or 90-100% confluency.

U-2 OS cells were washed with 5.0 mL 1×PBS, harvested with 2.0 mL trypsin-EDTA buffer, and brought up to ~1.0E6 cells/mL with 8.0 mL complete growth medium. Cells were diluted to ~1.0E5/mL in either treated medium (1:10 resuspended cells to treated medium) or growth medium (control). Diluted cells were seeded at a density of ~25 cells/mm$^2$ in each well of a 12-well tissue culture plate in the presence or absence of a 3D printed ring or disc (15 mm outer diameter, 2 mm height). Cells were grown at 37° C., 5% $CO_2$ for 24 hours. The medium in each well was replaced with fresh treated or control medium as appropriate, and cells were grown for an additional 24 hours. Images of cultured cells were captured directly from plates by wide field microscopy using phase contrast at 100× magnification on a NIKON® Eclipse T.i instrument (Nikon Corporation, Tokyo, Japan) via NIS-ELEMENTS® software v. 4.12 (Nikon Corporation, Tokyo, Japan).

The 3D printed polymer was tested in a PBS solution and allowed to incubate at 37° C. for 36 days with a 1:5 ratio of polymer to PBS, with 1.5 mL of polymer used for incubation. The PBS solution was used due to its physiological equivalent pH value to an in vitro environment, and 36 days of incubation was used since the FDA recommends testing permanent implant devices for more than 30 days. Well samples included blank, deionized water, PBS, and PBS with incubated polymer at 96 hours, 144 hours, 192 hours, 336 hours, and 864 hours (36 days) of incubation time. One PBS tablet from CALBIOCHEM® (Merck KGAA, Darmstadt, Germany) was dissolved in a 1.0 L bottle to create the PBS solution.

The incubated solution was tested for fluorescence absorbance to determine if any chemicals were released into the solution. Absorbance was taken from 200 nm to 1000 nm wavelength to give a wide spectrum, with values taken every 10 nm. 250 µL of each solution was placed in each well. Test well samples included a blank, deionized (DI) water, PBS solution, and PBS solution incubated with the polymer, with a sample size of N=3 or N=1. FIGS. 13A-13F provide plots of optical density versus wavelength (nm) for the polymer leaching study (with polyamide six 3D printed material in PBS-containing solutions for incubation at 864 hours, 336 hours, 192 hours, 144 hours, 96 hours, and 48 hours, respectively). The polymer incubation in PBS solution tests showed positive initial results. The minimal change in data around the 200-300 nm wavelengths is caused by hydrolysis of the polyamide polymer. The chemicals that seem to be leaching between 200-300 nm are ε-caprolactam, adipic acid, and hexamethylenediamine or another linear aliphatic diamine. Since the data around 200-300 nm does not change as drastically as seen at 900-1000 nm, along with the minimal loss in mass, the lower wavelengths appear to not be as invasive as the substance causing the optical change at the higher wavelengths. This substance is seen in the PBS and DI water samples, demonstrating that the change in optical density at 970 nm is due to the presence of DI water. There is minimal change or increase in optical density when the polymer is incubated at 370° C. for 36 days, while 48 hours to 192 hours shows no change from the baseline reading of PBS-only solution.

Figure 14A:
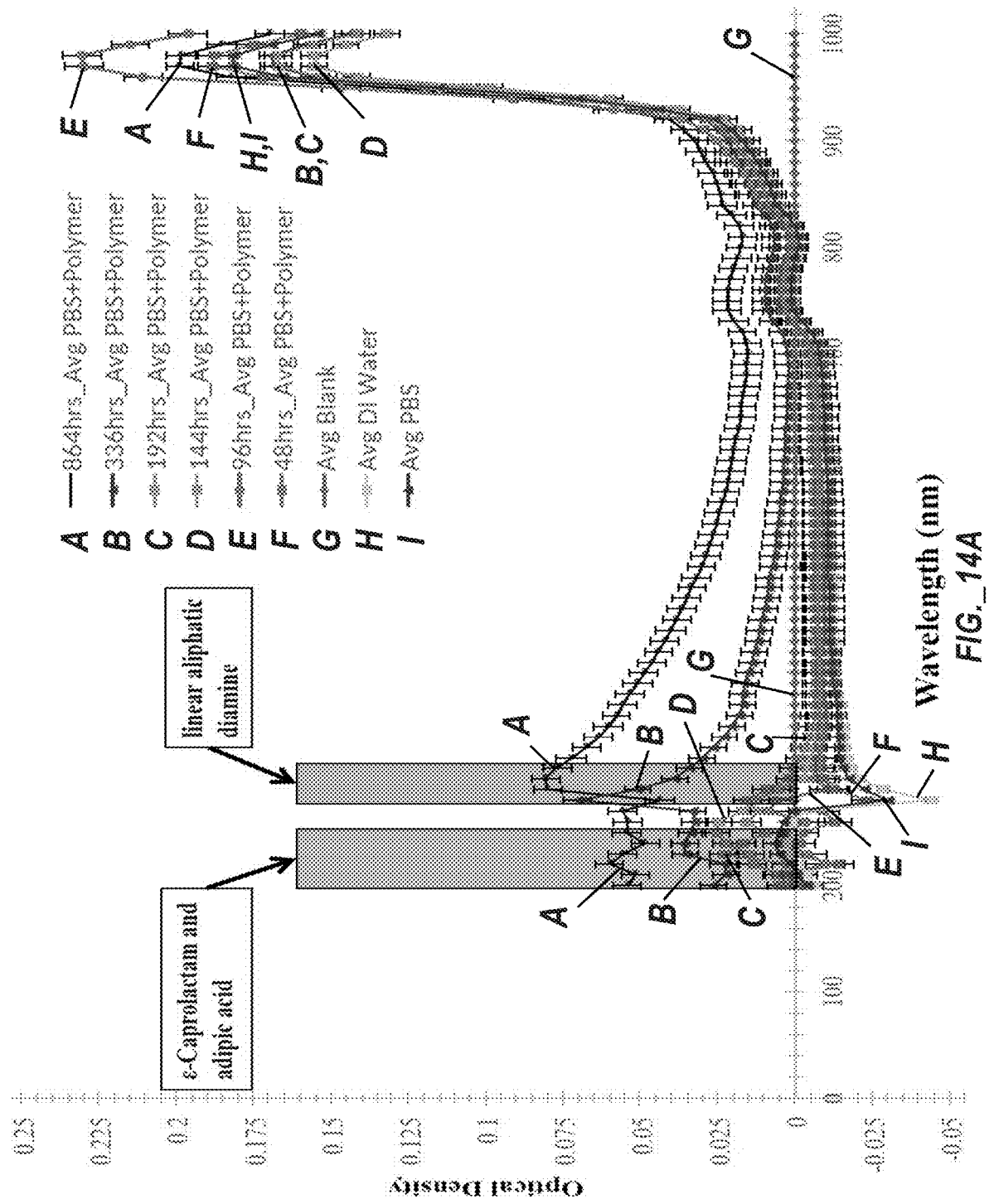
FIG. 14A is a plot of optical density versus wavelength (nm) for a polymer leaching study in a phosphate buffer solution for up to 864 hours and loss of mass from hydrolysis with a sample size of N=3, with error bars representing the standard deviation for each incubation period.

The polymer had a mass loss of 6.67 mg (0.415% of overall mass) caused by hydrolysis, where the polymer had an overall mass increase of 9.69% due to the absorption of DI water during incubation. The loss of mass was determined by dissolving a polymer sample in a toluene solution and then measuring the optical density with fluorescence absorbance and 250 µL of each solution into a 96-well plate. Results of such measurement are shown in FIGS. 14A and 14B. FIG. 14A is a plot of optical density versus wavelength (nm) for a polymer leaching study in a PBS solution for up to 864 hours and with loss of mass from hydrolysis. The solution was heated at 150° C. for 48 hours, with 11.5 mg of the polymer in powder form with 1000.0 mg of toluene. From here, using the density of 1.0715 g/mL, the results were used to calibrate the incubation test curve at 864 hours and determine the mass loss from hydrolysis. FIG. 14B is a plot of optical density versus wavelength (nm) for dissolved polymer powder in toluene versus neat toluene to determine the impact of chemical leaching into the solution. The polymer in the toluene solution had an optical density change of 0.12 from neat toluene, which when compared to the optical density of 0.07 for the 864 hours incubation study results in a mass loss of 6.67 mg, according to the plot shown in FIG. 14C, which plots optical density versus mass for 11.5 mg of powdered polymer dissolved in toluene at 280 nm wavelength.

With reference to FIGS. 14A and 14B, the increase in optical density from 200-300 nm is seen after incubating for 336 hrs or longer, indicating that the change is not due to drastic polymer breakdown/leaching. In contrast, incubation at 192, 144, 96, and 48 hours showed no change from the baseline PBS solution indicating that during the cytotoxicity testing, no additional chemicals were leached into the mediums. Additionally, the pH level did not alter after the polymer was incubated and stayed at a constant pH level of 7.4 or neutral.

To prepare samples for flow cytometry, cells were washed with 0.5 mL 1×PBS, harvested with 0.25 mL trypsin-EDTA buffer, and re-suspended with 0.75 mL growth medium. Cells were pelleted at 200×g for 5 minutes and re-suspended in 0.5 mL 1×PBS. A dead cell control sample was generated by incubating one of the untreated samples at 65° C. for 10 minutes. All samples were stained with 1.0 μL green fluorescent (SYTOX®) dye (S34860; Molecular Probes, Inc., Eugene, Oreg., USA) swirled to mix, and incubated at room temperature for 20 minutes. Stained samples were passed through 35 μm strainers into 6 mL tubes analyzed using a BD ACCURI® C6 flow cytometer with CFlow Plus software (Beckton, Dickinson and Company, Franklin Lakes, N.J., USA). Raw data FCS files were processed using FLOWJO® v.10.1 (FlowJo, LLC, Ashland, Oreg., USA).

Separately, 48 hours after inoculation, the wells were imaged to look for visible indicators of cell death. In FIGS. 15A and 15B we can see that the control group (in FIG. 15A), which contained the control medium and osteo cells, and the test group (in FIG. 15B), which contained test medium and osteo cells, had similar morphologies and levels of cell adhesion. The images show that there is little to no increase in cell death compared to the control groups across the entire well. If cell death were to be present, there would be large voids or blank areas in the well where the dead cell(s) became detached from the well bottom. The results shown in FIGS. 15A and 15B indicate that leached medium does not impede cell proliferation.

After imaging, the medium and cells were removed from each well, placed in a test tube, re-suspended, and a green fluorescence dye (SYTOX®) was used to stain the samples to determine the proportion of live and dead cells in each sample. The fluorescent dye does not diffuse across intact membranes of viable cells. Therefore the dye only concentrates within dead cells with permeable membranes. From here, the samples were transferred to a flow cytometry machine to record the fluorescence intensity. The machine is able to detect forward and side scatter, allowing it to detect cells that are in different orientations during testing. Using live cells and dead cells to determine the SYTOX® frequency range was first needed as the control for determining the cell count for future tests. Live cells were kept at 37° C. while (according to a control experiment) dead cells were fabricated by incubating the cells at 65° C. to kill them. Once the control cell count was performed, the control medium and test medium samples were tested.

FIG. 15C is a scatter plot showing forward scatter (a.u.) versus side scatter (a.u.) for flow cytometry analysis of U-2 OA control cells or cells killed with a high-temperature incubation, utilizing ~10,000 cells per sample, and excluding non-cellular particles. The dead cell sample showed lower forward scatter and higher side scatter signal, a typical indicator of cell death. The dead cell sample also produced a SYTOX® signal that was well above background, by about two orders of magnitude. These data were used to set a SYTOX® threshold gate (histogram of FIG. 15D) to distinguish live (L) and dead (D) cells in the experimental sample set. FIG. 15D provides superimposed histograms showing average proportions of U-2 OA live (L) and dead (D) cells determined by the SYTOX® signal threshold for the control cells or cells killed with a high-temperature incubation according to FIG. 15C. FIG. 15E is a bar chart showing average proportions for U-2 OA live and dead cells (~5,000 per sample) determined by the SYTOX® signal threshold (with bar gates) for cells in control medium, in test medium, in test medium plus disc material, and in test medium plus ring material. The average control medium and test medium samples show little difference in live and dead cell counts, with similar error bars. Restated, the proportion of live and dead cells did not vary significantly from the control for cell populations that were exposed to test medium or to solid samples of the 3D printed material (disc or ring-shaped). This demonstrates that the FFF 3D printed polymer has no significant impact or any toxic leaching that would cause death to the osteo cells.

It was observed that the 3D printed polymer showed no effect on the health of the human osteo cells. Imaging results showed no change in living cells when comparing the cells placed in either the control or test medium. There was observed cell death in the wells where the 3D printed discs were placed due to mechanical abrasion against the cells. The flow cytometry results showed no changes in live versus dead cell count trends when comparing the test medium to control medium samples.

The PBS incubation testing showed that after up to 192 hours there was no change in optical density—indicating that for the cytotoxicity testing, there were no additional substances released from the FFF 3D polymer. The pH level also stayed the same after 864 hours of incubation, demonstrating that the polymer does not affect the solution's acidity level. However, at 864 hours of incubation there were some changes in optical density around 200-300 nm wavelengths that appear to be due to minimal leaching of ε-Caprolactam, adipic acid, and hexamethylenediamine or another linear aliphatic diamine. Future studies may determine the exact chemicals that are leaching into the PBS solution and performing cytotoxicity on each chemical to determine if it is harmful to human bone, muscle, and skin cells. Additionally, there was a small mass loss due to hydrolysis of the polyamide six-based polymer of 6.67 mg, or 0.415% of overall mass.

Since the above-described study was limited to the osteo cell line, future toxicity testing may involve testing with skeletal muscle and skin cells. Skin cell testing would be beneficial because the tool interface portion of an osseointegratable prosthetic device disclosed herein protrudes through a patient's skin, and muscle cell testing would be beneficial since the abutment makes contact with those cells present outside a bone. Skin helps prevent infection in the body by creating a barrier between the body and outside environment; therefore testing of these cells would also be beneficial.

The minimal decrease in fixation strength from a simulated to cadaver environment along with the cytotoxicity and PBS incubation studies demonstrate that the devices disclosed herein show initial positive results for long-term implantation and as a stable fixation system for upper limb prosthetics.

The polyamide six-based material disclosed in the present application has strong inter-chain interactions caused by the hydrogen bonds between molecular chains of polyamide six, allowing it to be resistant to leaching. However, due to the hydrolysis experienced by the polymer, certain embodiments may benefit from using one or more polyamide polymers having longer chain lengths. Longer chain lengths include polyamide 10, 11, and 12, which are still thermoplastic and have higher mechanical properties then polyamide six materials. Use of such materials would allow 3D osseointegratable devices to still be manufactured on a FFF 3D printer while having a stronger resistance to hydrolysis and stronger mechanical properties. Thus, polyamide 10, 11, and 12 polymers are specifically contemplated for use in fabricating 3D printed osseointegratable devices as disclosed herein, since additional cross-linking of these polymers may inhibit or otherwise reduce chemical leaching. Other materials may be used, as will be recognized by one skilled in the art.

Upon reading the foregoing description in light of the accompanying drawing figures, those skilled in the art will understand the concepts of the disclosure and will recognize applications of these concepts not particularly addressed herein. Those skilled in the art will recognize improvements and modifications to the preferred embodiments of the present disclosure. All such improvements and modifications are considered within the scope of the concepts disclosed herein and the claims that follow.

What is claimed is:

1. An osseointegratable prosthetic device comprising:
   a body structure comprising an insertion end and an external interface end;
   an externally threaded anchor portion proximate to the insertion end, the externally threaded anchor portion comprising a shaft and a thread protruding from the shaft;
   a tool interface portion comprising at least one tool-receiving surface proximate to the external interface end; and
   a scaffold portion comprising a plurality of recesses configured to permit ingrowth of skeletal tissue, wherein the scaffold portion is arranged between the externally threaded anchor portion and the tool interface portion, and wherein the scaffold portion comprises a diameter no greater than a diameter of the externally threaded anchor portion;
   wherein the body structure further comprises a longitudinal core extending between the externally threaded anchor portion and the tool interface portion, the longitudinal core comprises a diameter that is smaller than a diameter of the shaft, and the plurality of recesses are bounded in part by exposed portions of the longitudinal core.

2. The osseointegratable prosthetic device of claim 1, further comprising a plurality of longitudinal fins extending outward from the longitudinal core and extending between the externally threaded anchor portion and the tool interface portion, wherein the plurality of longitudinal fins comprises externally threaded peripheral surfaces.

3. The osseointegratable prosthetic device of claim 2, wherein the plurality of longitudinal fins comprises at least three longitudinal fins.

4. The osseointegratable prosthetic device of claim 2, further comprising a plurality of apertures defined in the plurality of longitudinal fins.

5. The osseointegratable prosthetic device of claim 1, wherein:
   the osseointegratable prosthetic device further includes a plurality of transverse ribs extending radially outward from the longitudinal core.

6. The osseointegratable prosthetic device of claim 1, further comprising a flange portion arranged between the tool interface portion and the scaffold portion, wherein the flange portion comprises a maximum transverse dimension that exceeds a maximum transverse dimension of the scaffold portion.

7. The osseointegratable prosthetic device of claim 6, wherein the flange portion comprises a first radially extending flange element, and a second radially extending flange element that is discontinuous relative to the first radially extending flange element.

8. The osseointegratable prosthetic device of claim 1, wherein the body structure comprises a polymeric material.

9. The osseointegratable prosthetic device of claim 1, wherein the body structure comprises a thermoplastic material.

10. The osseointegratable prosthetic device of claim 1, wherein the body structure comprises a polyamide material.

11. The osseointegratable prosthetic device of claim 1, wherein the body structure embodies a unitary, fused polymeric body structure.

12. The osseointegratable prosthetic device of claim 1, wherein at least some recesses of the plurality of recesses contain porous material.

13. The osseointegratable prosthetic device of claim 1, wherein at least some recesses of the plurality of recesses contain organic material.

14. The osseointegratable prosthetic device of claim 1, wherein at least some recesses of the plurality of recesses contain cellular material.

15. A method of fabricating an osseointegratable prosthetic device according to claim 1, the method comprising:
    heating a thermoplastic material to a flowable state; and
    selectively depositing the heated thermoplastic material in sequential layers to form the body structure including the externally threaded anchor portion, the tool interface portion, and the scaffold portion;
    wherein the body structure embodies a unitary, fused polymeric body structure.

16. The method of claim 15, wherein prior to the heating, the thermoplastic material comprises a thermoplastic filament.

17. The method of claim 15, further comprising supplying at least one material to at least some recesses of the plurality of recesses, wherein the at least one material comprises one or more of a porous material, an organic material, or a cellular material.

18. A method of fabricating an osseointegratable prosthetic device according to claim 1, the method comprising:
    selectively depositing at least one layer of structural material;
    supplying energy to the at least one layer of structural material to fuse the at least one layer of structural material to an underlying layer of structural material; and
    repeating the selective deposition and energy supplying steps to form the body structure including the externally threaded anchor portion, the tool interface portion, and the scaffold portion.

19. The method of claim 18, wherein the at least one layer of structural material comprises a resin, and the energy supplying step comprises impinging photonic energy on the at least one layer of structural material.

20. The method of claim 18, wherein the at least one layer of structural material comprises a powder, and the energy supplying step comprises impinging laser emissions on the at least one layer of structural material.

21. The method of claim 20, wherein the powder comprises a metal.

22. The method of claim 20, wherein the powder comprises a polymeric material.

23. The method of claim 18, further comprising supplying at least one material to at least some recesses of the plurality of recesses, wherein the at least one material comprises one or more of a porous material, an organic material, or a cellular material.

24. A method for facilitating attachment of a prosthetic limb to a mammalian user, the method comprising:
    defining a cavity in a bone of the mammalian user; and
    threading the osseointegratable prosthetic device of claim 1 into the cavity.

* * * * *